US009023402B2

(12) United States Patent
Haas et al.

(10) Patent No.: US 9,023,402 B2
(45) Date of Patent: May 5, 2015

(54) METHOD FOR TREATING A MAMMAL BY ADMINISTRATION OF A COMPOUND HAVING THE ABILITY TO RELEASE CO

(75) Inventors: Werner E. Haas, Oeiras (PT); Carlos C. Romao, Cascias (PT); Beatriz Royo, Oeiras (PT); Ana Cristina Fernandes, Amadora (PT); Isabel Goncalves, Frente (PT)

(73) Assignee: ALFAMA—Investigação e Desenvolvimento de Produtos Farmacêuticos, Lda., Oeiras (PT)

( * ) Notice: Subject to any disclaimer, the term of this patent is extended or adjusted under 35 U.S.C. 154(b) by 0 days.

(21) Appl. No.: 13/078,735

(22) Filed: Apr. 1, 2011

(65) Prior Publication Data

US 2011/0237546 A1 Sep. 29, 2011

Related U.S. Application Data

(60) Continuation of application No. 11/453,319, filed on Jun. 14, 2006, now Pat. No. 7,964,220, which is a division of application No. 11/288,670, filed on Nov. 29, 2005, now abandoned, which is a division of application No. 10/356,738, filed on Feb. 3, 2003, now Pat. No. 7,011,854.

(60) Provisional application No. 60/353,233, filed on Feb. 4, 2002.

(51) Int. Cl.
| | |
|---|---|
| *A61K 33/00* | (2006.01) |
| *A61K 33/24* | (2006.01) |
| *A61K 31/28* | (2006.01) |
| *A61K 31/665* | (2006.01) |
| *A61K 31/67* | (2006.01) |
| *A61K 31/675* | (2006.01) |
| *C07F 17/00* | (2006.01) |
| *A61K 31/00* | (2006.01) |
| *A61K 31/555* | (2006.01) |
| *A61K 31/60* | (2006.01) |
| *A61K 31/603* | (2006.01) |
| *A61K 31/616* | (2006.01) |
| *A61K 31/695* | (2006.01) |
| *A61K 31/7048* | (2006.01) |
| *A61K 31/7135* | (2006.01) |
| *A61K 33/14* | (2006.01) |
| *A61K 33/32* | (2006.01) |
| *A61K 45/06* | (2006.01) |
| *A61K 47/48* | (2006.01) |
| *C07F 11/00* | (2006.01) |
| *C07F 13/00* | (2006.01) |
| *C07F 15/02* | (2006.01) |

(52) U.S. Cl.
CPC ............... *C07F 17/00* (2013.01); *A61K 31/00* (2013.01); *A61K 31/28* (2013.01); *A61K 31/555* (2013.01); *A61K 31/60* (2013.01); *A61K 31/603* (2013.01); *A61K 31/616* (2013.01); *A61K 31/695* (2013.01); *A61K 31/7048* (2013.01); *A61K 31/7135* (2013.01); *A61K 33/00* (2013.01); *A61K 33/14* (2013.01); *A61K 33/32* (2013.01); *A61K 45/06* (2013.01); *A61K 47/48015* (2013.01); *C07F 11/005* (2013.01); *C07F 13/005* (2013.01); *C07F 15/02* (2013.01); *Y10S 514/825* (2013.01); *Y10S 514/929* (2013.01); *Y10S 514/826* (2013.01); *Y10S 514/887* (2013.01); *Y10S 514/894* (2013.01); *Y10S 514/903* (2013.01); *Y10S 514/886* (2013.01); *Y10S 514/824* (2013.01); *Y10S 514/879* (2013.01); *Y10S 514/959* (2013.01); *Y10S 514/964* (2013.01); *Y10S 514/921* (2013.01); *Y10S 514/958* (2013.01); *Y10S 514/95* (2013.01)

(58) Field of Classification Search
USPC .............. 424/617, 646, 655, 699; 514/96, 97, 514/184, 185, 492, 824, 825, 826, 879, 886, 514/887, 894, 903, 921, 929
See application file for complete search history.

(56) References Cited

U.S. PATENT DOCUMENTS

| | | | |
|---|---|---|---|
| 2,870,180 | A | 1/1959 | Kozikowski et al. |
| 3,065,250 | A | 11/1962 | Levering |
| 3,278,570 | A | 10/1966 | Wilkinson et al. |
| 3,694,232 | A | 9/1972 | Hall et al. |
| 3,812,166 | A | 5/1974 | Wiechert et al. |

(Continued)

FOREIGN PATENT DOCUMENTS

| | | |
|---|---|---|
| DE | 4014762 A1 | 11/1991 |
| EP | 0 034 238 | 8/1981 |
| EP | 0076493 | 4/1983 |
| EP | 0 181 721 | 5/1986 |
| EP | 0 632 026 | 1/1995 |

(Continued)

OTHER PUBLICATIONS

Foresti, R. et al., "Use of carbon monoxide as a therapeutic agent: promises and challenges," Intensive Care Med., vol. 36, pp. 649-658 (2008).*

(Continued)

*Primary Examiner* — John Pak
(74) *Attorney, Agent, or Firm* — Wolf, Greenfield & Sacks, P.C.

(57) ABSTRACT

Several classes of in vivo carbon monoxide-releasing compounds are useful for the treatment and/or prevention of diseases, such as chronic inflammatory, e.g., rheumatoid arthritis, and of diseases with a strong inflammatory component, such as atherosclerosis, stroke, coronary disease, and Alzheimers disease. The in vivo carbon monoxide-releasing compounds can be attached to known drug vectors and/or known anti-inflammatory drugs, such as aspirin.

7 Claims, No Drawings

(56) References Cited

U.S. PATENT DOCUMENTS

| | | |
|---|---|---|
| 3,829,504 A | 8/1974 | Hall et al. |
| 3,980,583 A | 9/1976 | Mitchell et al. |
| 4,189,487 A | 2/1980 | Klosa |
| 4,312,989 A | 1/1982 | Spielvogel et al. |
| 4,322,411 A | 3/1982 | Vinegar et al. |
| 4,535,167 A | 8/1985 | Freidinger |
| 4,613,621 A | 9/1986 | Hormann |
| 4,649,151 A | 3/1987 | Dougherty et al. |
| 4,657,902 A | 4/1987 | Kappas et al. |
| 4,668,670 A | 5/1987 | Ridoeout et al. |
| 4,699,903 A | 10/1987 | Ridoeout et al. |
| 4,709,083 A | 11/1987 | Spielvogel |
| 4,792,452 A | 12/1988 | Howard et al. |
| 4,910,211 A | 3/1990 | Imamura et al. |
| 4,938,949 A | 7/1990 | Borch et al. |
| 5,010,073 A | 4/1991 | Kappas et al. |
| 5,086,060 A | 2/1992 | Haley et al. |
| 5,102,670 A | 4/1992 | Abraham et al. |
| 5,254,706 A | 10/1993 | Spielvogel et al. |
| 5,312,816 A | 5/1994 | Spielvogel et al. |
| 5,350,767 A | 9/1994 | Hallberg et al. |
| 5,447,939 A | 9/1995 | Glasky et al. |
| 5,621,000 A | 4/1997 | Arena et al. |
| 5,631,284 A | 5/1997 | Legzdins et al. |
| 5,659,027 A | 8/1997 | Spielvogel et al. |
| 5,664,563 A | 9/1997 | Schroeder et al. |
| 5,670,664 A | 9/1997 | Kao et al. |
| 5,700,947 A | 12/1997 | del Soldato |
| 5,756,492 A | 5/1998 | Buelow et al. |
| 5,767,157 A | 6/1998 | Van Moerkerken |
| 5,801,184 A | 9/1998 | Glasky et al. |
| 5,811,463 A | 9/1998 | Legzdins et al. |
| 5,824,673 A | 10/1998 | Abrams et al. |
| 5,861,426 A | 1/1999 | del Soldato et al. |
| 5,882,674 A | 3/1999 | Herrmann et al. |
| 5,885,621 A | 3/1999 | Head et al. |
| 5,888,982 A | 3/1999 | Perrella et al. |
| 5,891,689 A | 4/1999 | Takle et al. |
| 6,025,376 A | 2/2000 | Laurent et al. |
| 6,025,394 A | 2/2000 | Menander et al. |
| 6,027,936 A | 2/2000 | Glasky et al. |
| 6,040,341 A | 3/2000 | del Soldato et al. |
| 6,051,576 A | 4/2000 | Ashton et al. |
| 6,060,467 A | 5/2000 | Buelow et al. |
| 6,066,333 A | 5/2000 | Willis et al. |
| 6,177,471 B1 | 1/2001 | Menander et al. |
| 6,203,991 B1 | 3/2001 | Nabel et al. |
| 6,211,233 B1 | 4/2001 | del Soldato |
| 6,218,417 B1 | 4/2001 | del Soldato |
| 6,242,432 B1 | 6/2001 | del Soldato |
| 6,251,927 B1 | 6/2001 | Lai et al. |
| 6,284,752 B1 | 9/2001 | Abrams et al. |
| 6,331,564 B1 | 12/2001 | Brugnara et al. |
| 6,338,963 B1 | 1/2002 | Glasky et al. |
| 6,344,178 B1 | 2/2002 | Alberto et al. |
| 6,350,752 B1 | 2/2002 | Glasky et al. |
| 6,417,182 B1 | 7/2002 | Abrams et al. |
| 6,518,269 B1 | 2/2003 | Camden et al. |
| 6,645,938 B2 | 11/2003 | Oeltgen et al. |
| 6,673,908 B1 | 1/2004 | Stanton |
| 7,011,854 B2 | 3/2006 | Haas et al. |
| 7,045,140 B2 | 5/2006 | Motterlini et al. |
| 7,053,242 B1 | 5/2006 | Alberto et al. |
| 7,569,214 B2 | 8/2009 | Kozlowski |
| 7,964,220 B2 | 6/2011 | Haas et al. |
| 7,968,605 B2 | 6/2011 | de Matos et al. |
| 7,989,650 B2 | 8/2011 | Motterlini et al. |
| 8,236,339 B2 | 8/2012 | Motterlini et al. |
| 8,389,572 B2 | 3/2013 | Motterlini et al. |
| 2002/0045611 A1 | 4/2002 | Abrams et al. |
| 2002/0049190 A1 | 4/2002 | Bridger et al. |
| 2002/0043595 A1 | 8/2002 | Bridgers |
| 2002/0155166 A1 | 10/2002 | Choi et al. |
| 2002/0165242 A1 | 11/2002 | Glasky et al. |
| 2002/0193363 A1 | 12/2002 | Bridger et al. |
| 2003/0039638 A1 | 2/2003 | Bach et al. |
| 2003/0064114 A1 | 4/2003 | Motterlini et al. |
| 2003/0068387 A1 | 4/2003 | Buelow et al. |
| 2003/0124157 A1 | 7/2003 | Engles et al. |
| 2003/0157154 A1 | 8/2003 | Fuller et al. |
| 2003/0207786 A1 | 11/2003 | Miracle et al. |
| 2003/0219496 A1 | 11/2003 | Otterbein et al. |
| 2003/0219497 A1 | 11/2003 | Otterbein et al. |
| 2004/0052866 A1 | 3/2004 | Otterbein et al. |
| 2004/0067261 A1 | 4/2004 | Haas et al. |
| 2004/0122091 A1 | 6/2004 | Dasseux et al. |
| 2004/0131602 A1 | 7/2004 | Buelow et al. |
| 2004/0131703 A1 | 7/2004 | Bach et al. |
| 2004/0143025 A1 | 7/2004 | Buelow et al. |
| 2004/0214900 A1 | 10/2004 | Forbes et al. |
| 2004/0228930 A1 | 11/2004 | Billiar et al. |
| 2004/0258772 A1 | 12/2004 | Otterbein et al. |
| 2005/0048133 A1 | 3/2005 | Pinsky et al. |
| 2005/0175555 A1 | 8/2005 | Stradi et al. |
| 2006/0115542 A1 | 6/2006 | Motterlini et al. |
| 2006/0127501 A1 | 6/2006 | Motterlini et al. |
| 2006/0147548 A1 | 7/2006 | Motterlini et al. |
| 2006/0148900 A1 | 7/2006 | Haas et al. |
| 2006/0233890 A1 | 10/2006 | Haas et al. |
| 2007/0049640 A1 | 3/2007 | Pavliv |
| 2007/0065485 A1 | 3/2007 | Motterlini et al. |
| 2007/0207217 A1 | 9/2007 | Haas et al. |
| 2007/0207993 A1 | 9/2007 | Haas et al. |
| 2007/0219120 A1 | 9/2007 | de Matos et al. |
| 2008/0026984 A1 | 1/2008 | de Matos et al. |
| 2010/0105770 A1 | 4/2010 | Motterlini et al. |
| 2010/0196516 A1 | 8/2010 | Nobre |
| 2011/0015263 A1 | 1/2011 | Motterlini et al. |
| 2011/0038955 A1 | 2/2011 | Rodrigues et al. |

FOREIGN PATENT DOCUMENTS

| | | |
|---|---|---|
| FR | 2816212 | 5/2002 |
| GB | 1107510 | 6/1965 |
| GB | 111872.8 | 7/2001 |
| GB | 227135.1 | 12/2002 |
| GB | 227138.5 | 12/2002 |
| GB | 2395431 | 5/2004 |
| GB | 2395432 A | 5/2004 |
| HU | 57595 | 12/1991 |
| HU | 211 084 | 10/1995 |
| WO | WO 85/04326 A1 | 10/1985 |
| WO | WO 91/01128 | 2/1991 |
| WO | WO 91/01301 | 2/1991 |
| WO | WO 92/03402 | 3/1992 |
| WO | WO 92/04905 | 4/1992 |
| WO | WO 93/05795 | 4/1993 |
| WO | WO 94/01413 | 1/1994 |
| WO | WO 94/22482 | 10/1994 |
| WO | WO 95/05814 | 3/1995 |
| WO | WO 95/09831 | 4/1995 |
| WO | WO 95/35105 A1 | 12/1995 |
| WO | WO 96/03125 | 2/1996 |
| WO | WO 96/09038 | 3/1996 |
| WO | WO 97/16405 | 5/1997 |
| WO | WO 97/36615 | 10/1997 |
| WO | WO 97/37644 | 10/1997 |
| WO | WO 98/09618 | 3/1998 |
| WO | WO 98/13058 | 4/1998 |
| WO | WO 98/29115 | 7/1998 |
| WO | WO 98/38179 | 9/1998 |
| WO | WO 98/48848 | 11/1998 |
| WO | WO 99/67231 | 12/1999 |
| WO | WO 00/10613 | 3/2000 |
| WO | WO 00/21965 A1 | 4/2000 |
| WO | WO 00/36113 | 6/2000 |
| WO | WO 00/56145 | 9/2000 |
| WO | WO 00/56743 | 9/2000 |
| WO | WO 00/61537 | 10/2000 |
| WO | WO 01/12584 | 2/2001 |
| WO | WO 01/16359 | 3/2001 |
| WO | WO 01/25243 | 4/2001 |
| WO | WO 01/28545 | 4/2001 |
| WO | WO 02/078684 | 10/2002 |

(56) References Cited

FOREIGN PATENT DOCUMENTS

| WO | WO 02/080923 | 10/2002 |
|---|---|---|
| WO | WO 02/092072 | 11/2002 |
| WO | WO 02/092075 A2 | 11/2002 |
| WO | WO 02/092075 A3 | 11/2002 |
| WO | WO 03/000114 | 1/2003 |
| WO | WO 03/066067 | 8/2003 |
| WO | WO 03/067598 | 8/2003 |
| WO | WO 03/072024 | 9/2003 |
| WO | WO 03/082850 A | 10/2003 |
| WO | WO 03/088923 | 10/2003 |
| WO | WO 03/088981 | 10/2003 |
| WO | WO 03/094932 | 11/2003 |
| WO | WO 03/096977 | 11/2003 |
| WO | WO 03/103585 | 12/2003 |
| WO | WO 2004/029033 | 4/2004 |
| WO | WO 2004/043341 | 5/2004 |
| WO | WO 2004/045598 | 6/2004 |
| WO | WO 2004/045599 | 6/2004 |
| WO | WO 2004/080420 | 9/2004 |
| WO | WO 2005/013691 A1 | 2/2005 |
| WO | WO 2005/090400 | 9/2005 |
| WO | WO 2006/012215 | 2/2006 |
| WO | WO 2007/073226 | 6/2007 |
| WO | WO 2007/085806 | 8/2007 |
| WO | WO 2008/003953 | 1/2008 |
| WO | WO 2008/069688 | 6/2008 |
| WO | WO 2008/130261 A1 | 10/2008 |
| WO | WO 2009/013612 A1 | 1/2009 |

OTHER PUBLICATIONS

De Backer, O. et al., "Mechanisms of relaxation by carbon monoxide-releasing molecule-2 in murine gastric fundus and jejunum," European Journal of Pharmacology, vol. 572, pp. 197-206 (2007).*

Wang, P. et al., "Syntheses and evaluation of drug-like properties of CO-releasing molecules containing ruthenium and group 6 metal," European Journal of Medicinal Chemistry, vol. 74, pp. 199-215 (2014).*

Aburaya et al., Heme oxygenase-1 protects gastric mucosal cells against non-steroidal anti-inflammatory drugs. J Biol Chem. Nov. 3, 2006;281(44):33422-32. Epub Aug. 31, 2006.

Beck et al., Metallkomplexe mit biologisch wichtigen liganden : XVIII. Histidinato-carbonyl-komplexe von molybdän und wolfram. J Organometallic Chemistry. May 27, 1980;191(1):73-7.

Brisdon et al., The preparation and charactisation of triμ—halogenohexacarbonyl-dimetallate(I) anions of manganese and rhenium. J Organometallic Chem. 1978;161:233-43.

De Backer et al., Mechanisms of relaxation by carbon monoxide-releasing molecule-2 in murine gastric fundus and jejunum. Eur J Pharmacol. Oct. 31, 2007;572(2-3):197-206. Epub Jun. 13, 2007.

Flemstrom et al., Gastroduodenal HCO3(-) transport: characteristics and proposed role in acidity regulation and mucosal protection. Am J Physiol. Mar. 1982;242(3):G183-93.

Sato et al., Heme oxygenase-1 or carbon monoxide prevents the inflammatory response associated with xenograft rejection. Acta Haematologica. 13th Symposium on Mol Biol Hematopoiesis and Treatment of Leukemia and Cancer. New York, NY. Jul. 14-18, 2000. Released Jul. 2000;103(Suppl1): Abstract 345, p. 87.

[No Author Listed] "supramolecule" IUPAC compendium of chemical terminology. 2nd Ed. 1997. Retrieved from the internet at www.iupac.org/goldbook/SO6153.pdf on May 8, 2006.

[No Author Listed] Biosis Chem Abstracts Database. Accession No. PREV200600414130. 2005. Otterbein et al., Cell Mol Biol (Noisy-le-grand). Oct. 3, 2005;51(5):433-40. Abstract.

[No Author Listed] Chemical Abstracts. 2002;137:119662. (FR2816212).

[No Author Listed] Chemical Abstracts. 2004;140:400075, (WO2004/043341).

[No Author Listed] Chemical Abstracts. 2004;141:270758. (Ryter et al.).

[No Author Listed] Chemical Abstracts. 2004;142:211995. (Stein et al.).

[No Author Listed], Solutions, emulsions, suspensions, and extractives. Remington's Pharmaceutical Science. 1985; 17th edition. Gennaro, ed. Ch. 84. p. 1511-2.

Abe et al., The effects of prostacyclin analog OP-41483 on normothermic liver ischemia and reperfusion injury in rats. Prostaglandins Leukot Essent Fatty Acids. Jun. 1993;48(6):417-22.

Abel et al., Anionic halogenopentacarbonyls of chromium, molybdenum, and tungsten. J Chem Soc. 1963:2068-70.

Abel et al., Carbonyl halides of manganese and some related compounds. J Chem Soc. 1959;Part 2:1501-5.

Abel et al., Reaction of molybdenum carbonyl with various halides: a potassium etherate salt. Chem Indust. Apr. 16, 1960;442.

Abraham et al., The biological significance and physiological role of heme oxygenase. Cell Physiol Biochem. 1996;6:129-68.

Adkison et al., Semicarbazone-based inhibitors of cathepsin K, are they prodrugs for aldehyde inhibitors? Bioorg Med Chem Lett. Feb. 15, 2006;16(4):978-83. Epub Nov. 15, 2005. Abstract only.

Akamatsu et al., Heme oxygenase-l-derived carbon monoxide protects hearts from transplant associated ischemia reperfusion injury. FASEB J. Apr. 2004;18(6):771-2. Epub Feb. 20, 2004.

Alberto et al., A novel organometallic aqua complex of technetium for the labeling of biomolecules: synthesis of [99mTc(OH2)3(CO)3]+ from [99mTcO4]- in aqueous solution and its reaction with a bifunctional ligand. J Am Chem Soc. 1998;120:7987-8. Epub Jul. 24, 1998.

Alberto et al., Synthesis and properties of boranocarbonate: a convenient in situ CO source for the aqueous preparation of [(99m)Tc(OH(2))3(CO)3]+. J Am Chem Soc. Apr. 4, 2001;123(13):3135-6. Epub Mar. 13, 2001.

Alessio et al., Carbonyl Derivatives of Chloride-Dimethyl Sulfoxide-Ruthenium(II) Complexes: Synthesis, Structural Characterization, and Reactivity of Ru(CO)x(DMSO)4-xCl2 Complexes (x=1-3). Inorg Chem. 1995;34(19):4722-34.

Alessio et al., Carbonyl Derivatives of Chloride-Dimethyl Sulfoxide-Ruthenium(III) Complexes: Synthesis, Crystal Structure, and Reactivity of [(DMSO)2H][trans-RuCl4(DMSO-O)(CO)] and mer,cis-RuCl3(DMSO-O)2(CO). Inorg Chem. 1995;34(19):4716-21.

Allanson et al., Ultraviolet a (320-400 nm) modulation of ultraviolet B (290-320 nm)-induced immune suppression is mediated by carbon monoxide. J Invest Dermatol. Mar. 3, 2005;124(3):644-50.

Allardyce et al., Development of organometallic (organo-transition metal) pharmaceuticals. Appl Organomet Chem. Jan. 2005;19:1-10.

Amersi et al., Ex vivo exposure to carbon monoxide prevents hepatic ischemia/reperfusion injury through p38 MAP kinase pathway. Hepatology. Apr. 2002;35(4):815-23.

Andreadis et al., Oxidative and nitrosative events in asthma. Free Radic Biol Med. Aug. 1, 2003;35(3):213-25. Review. Abstract only.

Angelici et al., Carboxamido carbonyl complexes of manganese(I). Inorg Chim Acta. Mar 1968;2:3-7. Abstract only.

Angelici, Preparation, characterization, and reactions of the cis-Dihalotetracarbonylmanganate(I) anions. Inorg Chem. Aug 1964;3(8):1099-1102.

Aujard et al., Tridemethylisovelleral, a potent cytotoxic agent. Bioorg Med Chem. Nov. 15, 2005;13(22):6145-50. Epub Aug. 1, 2005. Abstract only.

Bagul et al., Carbon monoxide protects against ischemia-reperfusion injury in an experimental model of controlled nonheartbeating donor kidney. Transplantation. Feb. 27, 2008;85(4):576-81.

Bani-Hani et al., Modulation of thrombin-induced neuroinflammation in BV-2 microglia by carbon monoxide-releasing molecule 3. J Pharmacol Exp Ther. Sep. 2006;318(3):1315-22. Epub Jun. 13, 2006.

Bannenberg et al., Therapeutic applications of the gaseous mediators carbon monoxide and hydrogen sulfide. Expert Opin Ther Pat. May 2009;19(5):663-82. Review.

Barkoudah et al., The permissive role of endothelial NO in CO-induced cerebrovascular dilation. Am J Physiol Heart Circ Physiol. Oct. 2004;287(4):H1459-65. Epub Jun. 10, 2004.

Bauer et al., Evidence for a functional link between stress response and vascular control in hepatic portal circulation. Am J Physiol. Nov. 1996;271(5 Pt 1):G929-35.

(56) References Cited

OTHER PUBLICATIONS

Bauerová et al., Role of reactive oxygen and nitrogen species in etiopathogenesis of rheumatoid arthritis. Gen Physiol Biophys. Oct. 1999;18 Spec No. 15-20. Review. Abstract only.

Beal, Oxidatively modified proteins in aging and disease. Free Radic Biol Med. May 1, 2002;32(9):797-803. Review. Abstract only.

Beaty et al., An in vitro model for the in vivo mobilization of cadmium by chelating agents using 113Cd-NMR spectroscopy. Chem Res Toxicol. Jul.-Aug. 1992;5(4):568-75. Abstract only.

Becker et al., Age-related changes in antibody-dependent cell-mediated cytotoxicity in mouse spleen. Isr J Med Sci. Feb. 1979;15(2):147-50.

Becker et al., NO-independent regulatory site of direct sGC stimulators like YC-1 and BAY 41-2272. BMC Pharmacol. 2001;1:13. Epub Dec. 28, 2001.

Berman et al., Sensitization and catalysis of light-induced decarbonylation of aldehydes. J Am Chem Soc. 1963;85(24):4010-4013.

Beutler, The effect of carbon monoxide on red cell life span in sickle cell disease. Blood. Aug. 1975;46(2):253-9.

Boissiere et al., Exercise and vasorelaxing effects of CO-releasing molecules in hypertensive rats. Med Sci Sports Exerc. Apr. 2006;38(4):652-9.

Botros et al., Interaction between endogenously produced carbon monoxide and nitric oxide in regulation of renal afferent arterioles. Am J Physiol Heart Circ Physiol. Dec. 2006;291(6):H2772-8. Epub Jul. 14, 2006.

Brashears et al., Effect of meat packaging technologies on the safety and spoilage-indicating characteristics of ground beef—Phase 1: safety characteristics. Jun.-Jul. 2006 National Cattleman's Beef Asscoiation. 22 pages. Available at www.fda.gov/ohrms/dockets/dockets/05p0459/05p-0459-c000009-01-vol2.pdf.

Brooks et al., The spoilage characteristics of ground beef packaged in high-oxygen and low-oxygen modified atmosphere packages. Proc. Reciprocal Meat Conference. University of Illinois at Urbana-Champaign. Jun. 18-21, 2005:61-5.

Brouard et al., Carbon monoxide generated by heme oxygenase 1 suppresses endothelial cell apoptosis. J Exp Med. Oct. 2, 2000;192(7):1015-25.

Brüne et al., Inhibition of platelet aggregation by carbon monoxide is mediated by activation of guanylate cyclase. Mol Pharmacol. Oct. 1987;32(4):497-504.

Bundgaard et al., Pro-drugs as delivery systems. Pharm Int. 1981;2:136-40.

Bundgaard et al., Pro-drugs as drug delivery systems XX. Oxazolidines as potential pro-drug types for β-aminoalcohols, aldehydes or ketones. Intl J Pharm. Feb. 1982;10(2):165-75. Abstract only.

Burgmayer et al., Synthesis and structure of a 7-coordinate molybdenum carbonyl fluoride derivative—Et4n Mo(Co)2(S2cnet2)2f. Inorganic Chem. 1985;24:2224-30.

Burleson et al., The effect of dyes used to evaluate the in situ, ex-vivo, and perfused kidney. Invest Urol. Nov. 1981;19(3):165-8. Abstract only. Accession No. PREV198273058212.

Campbell et al., Molecular targets in immune-mediated diseases: the case of tumour necrosis factor and rheumatoid arthritis. Immunol Cell Biol. Oct. 2003;81(5):354-66.

Carroll et al., Ligand abstraction in the reaction of aryldiazonium ions with some iron complexes containing coordinated cysteine, maleonitriledithiol, or triarylphosphine. Can J Chem. 1974;52:1914-22.

Cepinskas et al., Carbon monoxide liberated from carbon monoxide-releasing molecule CORM-2 attenuates inflammation in the liver of septic mice. Am J Physiol Gastrointest Liver Physiol, Jan. 2008; 294:G184-G191. Epub Nov. 8, 2007.

Chakravortty et al., Inducible nitric oxide synthase and control of intracellular bacterial pathogens. Microbes Infect. Jun. 2003;5(7):621-7. Review. Abstract only.

Chatterjee, Water-soluble carbon monoxide-releasing molecules: helping to elucidate the vascular activity of the 'silent killer'. Br J Pharmacol. Jun. 2004;142(3):391-3. Epub May 17, 2004.

Chauveau et al., Gene transfer of heme oxygenase-1 and carbon monoxide delivery inhibit chronic rejection. Am J Transplant. Aug. 2002;2(7):581-92.

Chlopicki et al., Carbon monoxide released by CORM-3 inhibits human platelets by a mechanism independent of soluble guanylate cyclase. Cardiovasc Res. Jul. 15, 2006;71(2):393-401. Epub Mar. 22, 2006.

Cihonski et al., Crown ethers in inorganic chemistry—preparation and characterization of group 6 pentacarbonyl hydroxides and fluorides. Inorganic Chem. 1975;14(7):1717-20.

Clark et al., Cardioprotective actions by a water-soluble carbon monoxide-releasing molecule. Circ Res. Jul. 25, 2003;93(2):e2-8. Epub Jul. 3, 2003.

Clark et al., Heme oxygenase-1-derived bilirubin ameliorates postischemic myocardial dysfunction. Am J Physiol Heart Circ Physiol. Feb. 2000;278(2):H643-51.

Clark et al., Measuring left ventricular function in the normal, infarcted and CORM-3-preconditioned mouse heart using complex admittance-derived pressure volume loops. J Pharmacol Methods Toxicol. Mar.-Apr. 2009;59(2):94-9.

Coburn et al., Endogenous carbon monoxide production in man. J Clin Invest. Jul. 1963;42(7):1172-8.

Coceani et al., Carbon monoxide formation in the ductus arteriosus in the lamb: implications for the regulation of muscle tone. Br J Pharmacol. Feb. 1997;120(4):599-608.

Coceani, Carbon monoxide in vasoregulation: the promise and the challenge. Circ Res. Jun. 23, 2000;86(12):1184-6. Review.

Cohen et al., Dithiobenzoatotetracarbonylmanganese(I). Inorg Chem. 1964;3(11):1641-42.

Conant et al., Trimethylacetaldehyde and dimethylethylacetaldehyde. J Am Chem Soc. Apr. 1929;51(4):1246-55.

Cotton et al., Dimethyl- and diethyldithiocarbamate complexes of some metal carbonyl compounds. Inorg Chem. Jun. 2, 1964;3(10):1398-1402.

Cotton et al., X-ray molecular structures of Mn(CO)5(O2CCF3) and Mn(CO)3(C5H5N)2(O2CCF3). Inorg Chem. 1981;20(4):1287-91.

Coville et al., Steric measurement of substituted cyclopentadiene ligands and the synthesis and proton NMR spectral analysis of [(.eta. 5-C5H4R)Fe(CO)(L)I] complexes with variable R. Organometallics. 1992;11(3):1082-90.

Crabtree, Immune and inflammatory responses to *Helicobacter pylori* infection. Scandinavian J Gastroenterology. 1996;31(s215):3-10. Abstract only.

De Backer et al., Role of the soluble guanylyl cyclase alpha1/alpha2 subunits in the relaxant effect of CO and CORM-2 in murine gastric fundus. Naunyn Schmiedebergs Arch Pharmacol. Nov. 2008;378(5):493-502. Epub Jun. 18, 2008.

De Backer et al., Water-soluble CO-releasing molecules reduce the development of postoperative ileus via modulation of MAPK/HO-1 signalling and reduction of oxidative stress. Gut. Mar. 2009;58(3):347-56. Epub Nov. 20, 2008.

De Filippo et al., Inductive effect in dithiocarbanate decomposition mechanism. J Org Chem. 1973;38(3):560-3.

Desmard et al., A carbon monoxide-releasing molecule (CORM-3) exerts bactericidal activity against *Pseudomonas aeruginosa* and improves survival in an animal model of bacteraemia. FASEB J. Apr. 2009;23(4):1023-31. Epub Dec. 18, 2008.

Desmard et al., Carbon monoxide reduces the expression and activity of matrix metalloproteinases 1 and 2 in alveolar epithelial cells. Cell Mol Biol (Noisy-le-grand). Sep. 30, 2005;51(4):403-8.

Dharmaraj, Ruthenium (II) complexes containing bidentate Schiff bases and their antifungal activity. Transition Metal Chemistry. 2001; 26(1-2): 105-109.

Di Pascoli et al., Chronic CO levels have [corrected] a beneficial effect on vascular relaxation in diabetes. Biochem Biophys Res Commun. Feb. 17, 2006;340(3):935-43. Epub Dec. 27, 2005. Erratum in: Biochem Biophys Res Commun. Mar. 14, 2006;342(3):1003.

(56) References Cited

OTHER PUBLICATIONS

Diamantis et al., Preparation and structure of ethylenediaminetetraacetate complexes of ruthenium(II) with dinitrogen, carbon monoxide, and other π-acceptor ligands. Inorg Chem. 1981;20:1142-50.

Douglas et al., Preparation of some group VI fluorometal carbonyl derivatives. J Organometal Chem. 1974;65:65-9.

Drew et al., Synthesis, spectral properties, and reactions of manganese and rhenium pentacarbonyl phosphine and phosphite cation derivatives and related complexes. Inorg. Chem. 1975;14(7):1579-84.

Dröge, Free radicals in the physiological control of cell function. Physiol Rev. Jan. 2002;82(1):47-95. Review.

Duchêne et al., Cyclodextrins in targeting. Application to nanoparticles. Adv Drug Deliv Rev. Mar. 1, 1999;36(1):29-40.

Duckers et al., Heme oxygenase-1 protects against vascular constriction and proliferation. Nat Med. Jun. 2001;7(6):693-8.

Durante, Heme oxygenase-1 in growth control and its clinical application to vascular disease. J Cell Physiol. Jun. 2003;195(3):373-82. Review.

Egli et al., Organometallic 99mTc-aquaion labels peptide to an unprecedented high specific activity. J Nucl Med. Nov. 1999;40(11):1913-7.

Elliott et al., Nitric oxide: a regulator of mucosal defense and injury. J Gastroenterol. Dec. 1998;33(6):792-803. Review. Abstract only.

El-Kholy, Catalysis by crown ether complexes—part III effect of cation on the catalytic activity of crown ether—alkali metal halide complexes in the liquid phase oxidation of ethylbenzene. Egypt J Chem. 1979;22(1):23-8.

Fairlamb et al., η-pyrone iron(0)carbonyl complexes as effective CO-releasing molecules (CO-RMs). Bioorg Med Chem Lett. Feb. 15, 2006;16(4):995-8. Epub Nov. 11, 2005.

Fang, Antimicrobial reactive oxygen and nitrogen species: concepts and controversies. Nat Rev Microbiol. Oct. 2004;2(10):820-32. Review. Abstract only.

Feldmann et al., Anti-TNF alpha therapy of rheumatoid arthritis: what have we learned? Annu Rev Immunol. 2001;19:163-96. Review.

Ferrándiz et al., Treatment with a CO-releasing molecule (CORM-3) reduces joint inflammation and erosion in murine collagen-induced arthritis. Ann Rheum Dis. Sep. 2008;67(9):1211-7. Epub Dec. 6, 2007.

Ferrier et al., FTIR spectrometric study of geometrical isomers of dicarbonyl ferrobiscyteinate influence of the counter cation.J Molec Struct. 1995;344(3):189-93.

Fischer et al., Methylpyridin-Chrom(O)-Tricarbonyl. Zeitschrift Fur Naturforschung Part-B-Chemie Biochemie Biophysik Biologie Und Verwandten Gebiete. 1959;14:736-7. English translation provided.

Fischer et al., Uber aromatenkomplexe von metallen .37. zur aromatenkomplexebildung des pyridins mit chromhexacarbonyl. Chemische berichte-recueil. 1960;93:1156-61. English abstract provided.

Fischer, Crystal structure of 1,4,7,10,13-pentaoxacylcopentadecane sodium bromide, C10H20BrNaO5. Zeitschrift fur kristallographie. 1996;211:827-8. English translation provided.

Fiumana et al., Carbon monoxide mediates vasodilator effects of glutamate in isolated pressurized cerebral arterioles of newborn pigs. Am J Physiol Heart Circ Physiol. Apr. 2003;284(4):H1073-9.

Foresti et al., Reviewing the use of carbon monoxide-releasing molecules (CO-RMs) in biology: implications in endotoxin-mediated vascular dysfunction. Cell Mol Biol (Noisy-le-grand). Sep. 30, 2005;51(4):409-23.

Foresti et al., The heme oxygenase pathway and its interaction with nitric oxide in the control of cellular homeostasis. Free Radic Res. Dec. 1999;31(6):459-75. Review.

Foresti et al., Vasoactive properties of CORM-3, a novel water-soluble carbon monoxide-releasing molecule. Br J Pharmacol. Jun. 2004;142(3):453-60. Epub May 17, 2004.

Frangogiannis et al., The inflammatory response in myocardial infarction. Cardiovasc Res. Jan. 2002;53(1):31-47. Review.

Friebe et al., Sensitizing soluble guanylyl cyclase to become a highly CO-sensitive enzyme. Embo J. Dec. 16, 1996;15(24):6863-8.

Friebe et al., YC-1 potentiates nitric oxide- and carbon monoxide-induced cyclic GMP effects in human platelets. Mol Pharmacol. Dec. 1998;54(6):962-7.

Fujita et al., Paradoxical rescue from ischemic lung injury by inhaled carbon monoxide driven by derepression of fibrinolysis. Nat Med. May 2001;7(5):598-604.

Fukuda et al., Induction of heme oxygenase-1 (HO-1) after traumatic brain injury in the rat. Neurosci Lett. Oct. 20, 1995;199(2):127-30.

Furchgott et al., Endothelium-dependent and -independent vasodilation involving cyclic GMP: relaxation induced by nitric oxide, carbon monoxide and light. Blood Vessels. 1991;28(1-3):52-61.

Giboreau et al., Procedure for the preparation of pure dithiocarbamates. J Org Chem. 1994;59:1205-7.

Girolami et al., Reaction of binuclear carboxylate complexes of molybdenum, rhenium, ruthenium, and rhodium with tert-Butyl Isocyanide: metal-metal bond cleavage vs. bond retention. Inorganic Chemistry. Jul. 1981;20(7):2040-4.

Gordeuk et al., Carbonyl iron therapy for iron deficiency anemia. Blood. Mar. 1986;67(3):745-52.

Gottschaldt et al., Sugar-selective enrichment of a D-glucose-substituted ruthenium bipyridyl complex inside HepG2 cancer cells. Chembiochem. Mar. 22, 2010;11(5):649-52. Epub Feb. 15, 2010.

Greener et al., Now you're signaling, with gas: gasotransmitters open a window on biology and drug development. The Scientist. 2004;18(17):20-2. Epub Sep. 13, 2004.

Günther et al., Carbon monoxide protects pancreatic beta-cells from apoptosis and improves islet function/survival after transplantation. Diabetes. Apr. 2002;51(4):994-9. Medline Abstract. Accession No. NLM11916917.

Guo et al., Administration of a CO-releasing molecule at the time of reperfusion reduces infarct size in vivo. Am J Physiol Heart Circ Physiol. May 2004;286(5):H1649-53. Epub Jan. 2, 2004.

Haag et al., Polymer therapeutics: concepts and applications. Angew Chem Int Ed Engl. Feb. 13, 2006;45(8):1198-215. Review. Abstract only.

Haddleton et al., [N-Alkyl-(2-pyridyl)methanimine]copper(I) complexes: characterisation and application as catalysts for atom-transfer polymerisation. Eur J Inorg Chem. Dec. 7, 1998;1998(11):1799-1806. Abstract only.

Haddleton et al., Atom transfer polymerization of methyl methacrylate mediated by alkylpyridylmethanimine type ligands, copper(I) bromide, and alkyl halides in hydrocarbon solution. Macromolecules. 1999;32(7):2110-19. Abstract only.

Hadjigogos, The role of free radicals in the pathogenesis of rheumatoid arthritis. Panminerva Med. Mar. 2003;45(1):7-13. Review. Abstract only.

Hall et al., DNA interaction with metal complexes and salts of substituted boranes and hydroborates in murine and human tumor cell lines. Anticancer Drugs. Aug. 1991;2(4):389-99.

Hall et al., The anti-inflammatory activity of boron derivatives in rodents. Met Based Drugs. 1995;2(1):1-12.

Hall et al., The anti-inflammatory activity of metal complexes and salts of amine carboxyboranes. Appl Organomett Chem. 1994;8:473-80.

Hall et al., The hypolipidemic activity of metal complexes of amine carboxyboranes in rodents. Met Based Drugs. 1994;1(4):329-36.

Hancock et al., Antibody-induced transplant arteriosclerosis is prevented by graft expression of anti-oxidant and anti-apoptotic genes. Nat Med. Dec. 1998;4(12):1392-6.

Henricks et al., Reactive oxygen species as mediators in asthma. Pulm Pharmacol Ther. 2001;14(6):409-20. Review. Abstract only.

Herrick et al., Flash photolytic investigation of photoinduced carbon monoxide dissociation from dinuclear manganese carbonyl compounds. Inorg Chem. 1984;23:4550-3.

Hieber et al., Derivate des Mangancarbonyls mit schwefelorganischen Liganden. Chemische Berichte. 1966;99(7):2312-21. English abstract provided.

Hitchon et al., Oxidation in rheumatoid arthritis. Arthritis Res Ther. 2004;6(6):265-78. Epub Oct. 13, 2004. Review.

Hogg, Free radicals in disease. Semin Reprod Endocrinol. 1998;16(4):241-8. Review. Abstract only.

(56) References Cited

OTHER PUBLICATIONS

Holmuhamedov et al., Mitochondrial ATP-sensitive K+ channels modulate cardiac mitochondrial function. Am J Physiol. Nov. 1998;275(5 Pt 2):H1567-76.
Hosgood et al., Application of nitric oxide and carbon monoxide in a model of renal preservation. Br J Surg. Aug. 2008;95(8):1060-7.
Huang et al., Photolysis of the histidine-heme-CO complex. J Am Chem Soc. Nov. 1, 1991;113:9141-4.
Huebers et al., Absorption of carbonyl iron. J Lab Clin Med. Nov. 1986;108(5):473-8.
Ignat'Ev et al., Reactivity of perfluoroakyl halides towards nucleophiles. Russ J Electrochem. Dec. 1995;31(12):1235-9. Translated from Elektrokhimiya. 1995;31(12):1337-42.
Jander et al., Neutralisationenanaloge reaktionen in essigaureanhybrid. Zietschrift fur anorganische chemie. 1948;255:238-52. English abstract provided.
Jellum et al., Quantitative determination of biologically important thiols and disulfides by gas-liquid chromatography. Analyt Biochem. 1969;31:339-47. Abstract only.
Johansen et al., Spectrophotometric determination of the rates of hydrolysis of aldehyde-releasing pro-drugs in aqueous solution and plasma. Intl J Pharma. Dec. 1982;13(1):89-98. Abstract only.
Johnson et al., Metal carbonyls as pharmaceuticals? [Ru(CO)3Cl(glycinate)], a CO-releasing molecule with an extensive aqueous solution chemistry. Dalton Trans. Apr. 21, 2007;(15):1500-8. Epub Mar. 8, 2007.
Johnson et al., Metal carbonyls: a new class of pharmaceuticals? Angew Chem Int Ed Engl. Aug. 18, 2003;42(32):3722-9.
Johnson et al., Role of endogenous carbon monoxide in central regulation of arterial pressure. Hypertension. Oct. 1997;30(4):962-7.
Józkowicz et al., Heme oxygenase and angiogenic activity of endothelial cells: stimulation by carbon monoxide and inhibition by tin protoporphyrin-IX. Antioxid Redox Signal. Apr. 2003;5(2):155-62.
Kamimura et al., The protective effect of carbon monoxide on the ischemia-induced cell death. The J Biochem. Aug. 2002;74(8):926. Japanese abstract. English translation provided.
Kharitonov et al., Basis of guanylate cyclase activation by carbon monoxide. Proc Natl Acad Sci U S A. Mar. 28, 1995;92(7):2568-71.
Kharitonov et al., Kinetics and equilibria of soluble guanylate cyclase ligation by CO: effect of YC-1. Biochemistry. Aug. 17, 1999;38(33):10699-706.
Krueger et al., Potential of tumor necrosis factor inhibitors in psoriasis and psoriatic arthritis. Arch Dermatol. Feb. 2004;140(2):218-25. Review.
Kubic et al., Metabolism of dihalomethanes to carbon monoxide. I. In vivo studies. Drug Metab Dispos. Jan.-Feb. 1974;2(1):53-7. Abstract only.
Kuiate et al., Composition of the essential oil from leaves and flowers of *Dichrocephala integrifolia* (L.) 0. Kuntze Chev. From Cameroon. Flavour and Fragrance J. Nov./Dec. 1999;14(6):419-20. Abstract only.
Lambert et al., O,O'-Diphenyldithiophosphatotetracarbonylmanganese(I) and related compounds. Inorg Chem. 1966;5(7):1287-9.
Lawton et al., Myocardial oxygen consumption in the rabbit heart after ischemia: hyperpolarized arrest with pinacidil versus depolarized hyperkalemic arrest. Circulation. Nov. 4, 1997;96(9 Suppl):II-247-52.
Ledger, Carbon monoxide-releasing metal carbonyls: a new class of pharmaceuticals? Drug Disc Today. Dec. 2003;8(23):1096.
Lee et al., Heme oxygenase-1 mediates the anti-inflammatory effect of interleukin-10 in mice. Nat Med. Mar. 2002;8(3):240-6.
Levrand et al., Controlled release of volatile aldehydes and ketones by reversible hydrazone formation—classical profragrances are getting dynamic. Chem. Commun. 2006;28:2965-7. Epub Apr. 3, 2006.
Li et al., Carbon monoxide protects PC12 cells from peroxynitrite-induced apoptotic death by preventing the depolarization of mitochondrial transmembrane potential. Biochem Biophys Res Commun. Apr. 14, 2006;342(3):984-90. Epub Feb. 20, 2006.

Lipmann et al., Organometallic Lewis Acids. LI. Reactivity of organometallic Lewis Acids (OC)4Re(OEt2)FBF3 and (OC)2(PPh3)2Ru(FBF3)2. Journal of Organometallic Chemistry. 1994;466(1-2):167-174. English abstract provided.
Loftsson et al., Cyclodextrins in topical drug formulations: theory and practice. Int J Pharm. Aug. 28, 2001;225(1-2):15-30. Review.
Loganson, Metal carbonyl complexes with ligands of biological origin. Russ Chem Rev. 1985;54(3):277-92.
Lovell et al., Biologic agents for the treatment of juvenile rheumatoid arthritis: current status. Pediatr Drugs. 2004;6(3):137-46.
Mahmoud et al., Potential anticancer agents. XVI. Isolation of bicyclofamesane sesquiterpenoids from *Capsicodendron dinisii*. J Nat Prod. May-Jun. 1980;43(3):365-71. Abstract only.
Mai et al., Soluble surface proteins from *Helicobacter pylori* activate monocytes/macrophages by lipopolysaccharide-independent mechanism. J Clin Invest. Mar. 1991;87(3):894-900.
Maines, Heme oxygenase: function, multiplicity, regulatory mechanisms, and clinical applications. FASEB J. Jul. 1988;2(10):2557-68. Review.
Maines, The heme oxygenase system: a regulator of second messenger gases. Annu Rev Pharmacol Toxicol. 1997;37:517-54. Review.
Marks et al.,. Does carbon monoxide have a physiological function? Trends Pharmacol Sci. May 1991;12(5):185-8. Review.
Martins et al., Induction of carbon monoxide in the donor reduces graft immunogenicity and chronic graft deterioration. Transplant Proc. Jan.-Feb. 2005;37(1):379-81.
Matsuda et al., Mediators of non-adrenergic non-cholinergic inhibitory neurotransmission in porcine jejunum. Neurogastroenterol Motil. Oct. 2004;16(5):605-12.
Mattes et al., Triply bridged thiobenzoato carbonyl manganates(I) and rhenates(I). The crystal and molecular structure of caesium tris(μ-thiobenzoatos(S))bis(tricarbonyl rhenate). J Organometall Chem. Sep. 25, 1979; 178(1):191-6.
McLaughlin et al., Potentiation of carbon monoxide-induced relaxation of rat aorta by YC-1 [3-(5'-hydroxymethyl-2'-furyl)-1-benzylindazole]. Can J Physiol Pharmacol. Apr. 2000;78(4):343-9.
McMillen et al., Hydrocarbon bond dissociation energies. Ann Rev Phys Chem. Oct. 1982;33:493-532.
Meder et al., Metallkomplexe mit biologisch wichtigen liganden, XLII [1] carbonylmetallkomplexe mit anionen von mehrfunktionellen alpha-aminosaeuren [Metal complexes with biologically important ligands], XLII [1] carbonyl metal complexes with anions of polyfunctional alpha-amino acids]. Zeitschrift fur Naturforschung;1986:1247-54. German language reference. English abstract provided.
Megías et al., The carbon monoxide-releasing molecule tricarbonyldichlororuthenium(II) dimer protects human osteoarthritic chondrocytes and cartilage from the catabolic actions of interleukin-1beta. J Pharmacol Exp Ther. Apr. 2008;325(1):56-61. Epub Jan. 14, 2008.
Miguel et al., Manganese(I) complexes with (tricyclohexylphosphonio)dithiocarboxylate as chelate and unidentate ligand. X-Ray crystal structure of fac-[Mn(CO)3{S2CP(C6H11)3}2]ClO4•H2O. J Chem Soc, Dalton Trans. 1987;12:2875-80.
Mikuls et al., Benefit-risk assessment of infliximab in the treatment of rheumatoid arthritis. Drug Saf. 2003;26(1):23-32. Review. Abstract only.
Miller et al., The pharmacological activities of the metabolites of N-[(trimethylamineboryl)-carbonyl]-L-phenylalanine methyl ester. Met Based Drugs. 1996;3(5):219-26.
Moncada et al., Nitric oxide: physiology, pathophysiology, and pharmacology. Pharmacol Rev. Jun. 1991;43(2):109-42.
Moncada et al., The discovery of nitric oxide and its role in vascular biology. Br J Pharmacol. Jan. 2006;147 Suppl 1:S193-201.
Moore et al., Brief inhalation of low-dose carbon monoxide protects rodents and swine from postoperative ileus. Crit Care Med. Jun. 2005;33(6):1317-26.
Morita et al., Carbon monoxide controls the proliferation of hypoxic vascular smooth muscle cells. J Biol Chem. Dec. 26, 1997;272(52):32804-9.

(56) References Cited

OTHER PUBLICATIONS

Morita et al., Endothelial cell expression of vasoconstrictors and growth factors is regulated by smooth muscle cell-derived carbon monoxide. J Clin Invest. Dec. 1995;96(6):2676-82.

Morita et al., Smooth muscle cell-derived carbon monoxide is a regulator of vascular cGMP. Proc Natl Acad Sci U S A. Feb. 28, 1995;92(5):1475-9.

Morse et al., Suppression of inflammatory cytokine production by carbon monoxide involves the JNK pathway and AP-1. J Biol Chem. Sep. 26, 2003;278(39):36993-8. Epub Jul. 11, 2003.

Motterlini et al., Bioactivity and pharmacological actions of carbon monoxide-releasing molecules. Curr Pharm Des. 2003;9(30):2525-39.

Motterlini et al., Carbon monoxide-releasing molecules: characterization of biochemical and vascular activities. Circ Res. Feb. 8, 2002;90(2):E17-24.

Motterlini et al., Chapter 16: Studies on the development of carbon-monoxide—releasing molecules: potential applications for the treatment of cardiovascular dysfunction. Ed., Rui Wang. CRC Press, New York. 2002:249-72.

Motterlini et al., Characterization of vasoactive effects elicited by carbon monoxide-releasing molecules. Abstracts 8th Intl Symposium on Mechanisms of Vasodilation. J Vasc Res. May 31-Jun. 3, 2001;055.

Motterlini et al., CORM-A1: a new pharmacologically active carbon monoxide-releasing molecule. FASEB J. Feb. 2005;19(2):284-6. Epub Nov. 19, 2004.

Motterlini et al., Functional and metabolic effects of propionyl-L-carnitine in the isolated perfused hypertrophied rat heart. Mol Cell Biochem. Oct. 21, 1992;116(1-2):139-45.

Motterlini et al., Heme oxygenase-1-derived carbon monoxide contributes to the suppression of acute hypertensive responses in vivo. Circ Res. Sep. 7, 1998;83(5):568-77. Correction included.

Motterlini et al., Therapeutic applications of carbon monoxide-releasing molecules. Expert Opin Investig Drugs. Nov. 2005;14(11):1305-18. Review.

Motterlini, Vasoactive properties of carbon monoxide-releasing molecules. Biomed Pharmacother. 2002;56(7):349-50.

Moya et al., Metal carbonyl complexes containing heterocyclic nitrogen ligands: Part IX. MnBr(CO)3(3,3'-R-2,2'-biquinoline) compounds. Polyhedron. Mar. 1, 2002; 21(4):439-44. Abstract only.

Mungrue et al., From molecules to mammals: what's NOS got to do with it? Acta Physiol Scand. Oct. 2003;179(2):123-35. Review. Abstract only.

Musameh et al., Improved myocardial function after cold storage with preservation solution supplemented with a carbon monoxide-releasing molecule (CORM-3). J Heart Lung Transplant. Nov. 2007;26(11):1192-8.

Musameh et al., Positive inotropic effects of carbon monoxide-releasing molecules (CO-RMs) in the isolated perfused rat heart. Br J Pharmacol. Dec. 2006;149(8):1104-12. Epub Oct. 23, 2006.

Nagai et al., Unusual CO bonding geometry in abnormal subunits of hemoglobin M Boston and hemoglobin M Saskatoon. Biochemistry. Jul. 2, 1991;30(26):6495-503.

Nakao et al., Carbon monoxide inhalation protects rat intestinal grafts from ischemia/reperfusion injury. Am J Pathol. Oct. 2003;163(4):1587-98.

Nakao et al., Protective effect of carbon monoxide in transplantation. J Cell Mol Med. Jul.-Sep. 2006;10(3):650-71. Review.

Nathan, Points of control in inflammation. Nature. Dec. 19-26, 2002;420(6917):846-52. Review.

Ndisang et al., Modulation of the immunological response of guinea pig mast cells by carbon monoxide. Immunopharmacology. Jun. 1999;43(1):65-73.

Neto et al., Protection of transplant-induced renal ischemia-reperfusion injury with carbon monoxide. Am J Physiol Renal Physiol. Nov. 2004;287(5):F979-89. Epub Aug. 3, 2004.

Nitschke et al., Properties of (trifluoromethanesulfonato)pentacarbonylmanganese(I) and—rhenium(I). Reactions in superacid solvents. Inorg Chem. 1985;24(13):1972-8.

Nobre et al., Antimicrobial action of carbon monoxide-releasing compounds. Antimicrob Agents Chemother. Dec. 2007;51(12):4303-7. Epub Oct. 8, 2007.

Nudelman et al., Prodrugs of butyric acid. Novel derivatives possessing increased aqueous solubility and potential for treating cancer and blood diseases. Eur J Med Chem. Jan. 2001;36(1):63-74. Abstract only.

Nudelman et al., The role of intracellularly released formaldehyde and butyric acid in the anticancer activity of acyloxyalkyl esters. J. Med. Chem. Feb. 24, 2005;48(4):1042-54. Epub Jan. 22, 2005. Abstract only.

Nydegger et al., New concepts in organ preservation. Transpl Immunol. May 2002;9(2-4):215-25.

O'Brien et al., Aldehyde sources, metabolism, molecular toxicity mechanisms, and possible effects on human health. Crit Rev Toxicol. Aug. 2005;35(7):609-62. Review.

Otterbein et al., Carbon monoxide has anti-inflammatory effects involving the mitogen-activated protein kinase pathway. Nat Med. Apr. 2000;6(4):422-8.

Otterbein et al., Carbon monoxide provides protection against hyperoxic lung injury. Am J Physiol. Apr. 1999;276(4 Pt 1):L688-94.

Otterbein et al., Carbon monoxide suppresses arteriosclerotic lesions associated with chronic graft rejection and with balloon injury. Nat Med. Feb. 2003;9(2):183-90. Epub Jan. 21, 2003.

Otterbein et al., Exogenous administration of heme oxygenase-1 by gene transfer provides protection against hyperoxia-induced lung injury. J Clin Invest. Apr. 1999;103(7):1047-54.

Otterbein et al., Heme oxygenase-1: unleashing the protective properties of heme. Trends Immunol. Aug. 2003;24(8):449-55. Review.

Otterbein, Carbon monoxide: innovative anti-inflammatory properties of an age-old gas molecule. Antioxid Redox Signal. Apr. 2002;4(2):309-19. Review.

Ozawa et al., Leydig cell-derived heme oxygenase-1 regulates apoptosis of premeiotic germ cells in response to stress. J Clin Invest. Feb. 2002;109(4):457-67.

Pae et al., Carbon monoxide produced by heme oxygenase-1 suppresses T cell proliferation via inhibition of IL-2 production. J Immunol. Apr. 15, 2004;172(8):4744-51.

Paintner et al., Synthesis and antimicrobial activity of tetrodecamycin partial structures. Bioorg Med Chem. Jul. 3, 2003;11(13):2823-33. Abstract only.

Pankey et al., Clinical relevance of bacteriostatic versus bactericidal mechanisms of action in the treatment of Gram-positive bacterial infections. Clin Infect Dis. Mar. 15, 2004;38(6):864-70. Epub Mar. 1, 2004. Review.

Patel et al., Preparation of (η5-cyclopentadienyl) and (η5-Methylcyclopentadienyl)Fe(CO)2Me cyclodextrin inclusion compounds and their subsequent ligand substitution reactions. Attempts at cyclodextrin mediated enantioselective ligand substitution. J Organomet Chem. 1997;547:103-112.

Peloso et al., Expanding the armamentarium for the spondyloarthropathies. Arthritis Res Ther. 2004;6 Suppl 2:S36-43. Epub Jun. 21, 2004.

Pena et al., A novel carbon monoxide-releasing molecule fully protects mice from severe malaria. Antimicrob Agents Chemother. Mar. 2012;56(3):1281-90. Epub Dec. 12, 20111.

Piantadosi, Biological chemistry of carbon monoxide. Antioxid Redox Signal. Apr. 2002;4(2):259-70. Review.

Pneumatikakis et al., Interactions of bis[µ-chloro-chlorotricarbonylruthenium(II) and poly-[µdichloro-dicarbonylruthenium (II)] with nucleotides. Inorg Chimica Acta. 1988;151:243-8.

Quick et al., Pentacarbonylmanganese halides. In Inorganic Syntheses, vol. 19. Duward F. Shriver., Ed. Inorganic Syntheses, Inc. 1979:158-63.

Rattan et al., Mechanism of internal anal sphincter relaxation by CORM-1, authentic CO, and NANC nerve stimulation. Am J Physiol Gastrointest Liver Physiol. Sep. 2004;287(3):G605-11.

(56) References Cited

OTHER PUBLICATIONS

Rehder et al., 55Mn NMR characteristics of carbonylmanganese complexes with hetero-substituted dithioformato-, thioformamido- and thioformamide ligands [1]. Inorg Chim Acta. 1983;73:243-7. Abstract only.

Reimann et al., Reactions of metal carbonyls. Part III. Steric and stereochemical limitations of higher substitution of manganese carbonyl bromide. J Chem Soc Dalton Trans. 1973;841-6. Abstract only.

Rodella et al., Carbon monoxide and biliverdin prevent endothelial cell sloughing in rats with type I diabetes. Free Radic Biol Med. Jun. 15, 2006;40(12):2198-205. Epub Mar. 20, 2006.

Rutkowska-Zbik et al., Theoretical density functional theory studies on interactions of small biologically active molecules with isolated heme group. J Comput Chem. Mar. 2007;28(4):825-31.

Ryan et al., Renal vascular responses to CORM-A1 in the mouse. Pharmacol Res. Jul. 2006;54(1):24-9. Epub Mar. 9, 2006.

Ryter et al., Carbon monoxide in biology and medicine. Bioessays. Mar. 2004;26(3):270-80.

Ryter et al., Carbon monoxide: to boldly go where NO has gone before. Sci STKE. Apr. 20, 2004;2004(230):RE6. Review.

Ryter et al., Heme oxygenase/carbon monoxide signaling pathways: regulation and functional significance. Mol Cell Biochem. May-Jun. 2002;234-235(1-2):249-63. Review.

Ryter et al., Heme oxygenase-1/carbon monoxide: from basic science to therapeutic applications. Physiol Rev. Apr. 2006;86(2):583-650. Review.

Sacerdoti et al., Treatment with tin prevents the development of hypertension in spontaneously hypertensive rats. Science. Jan. 20, 1989;243(4889):388-90.

Sacks et al., Comparative bioavailability of elemental iron powders for repair of iron deficiency anemia in rats. Studies of efficacy and toxicity of carbonyl iron. Am J Clin Nutr. Apr. 1978;31(4):566-71.

Salazar-Salinas et al., Molecular biosensor based on a coordinated iron complex. J Chem Phys. Mar. 14, 2009;130(10):105101.

Sammut et al., Carbon monoxide is a major contributor to the regulation of vascular tone in aortas expressing high levels of haeme oxygenase-1. Br J Pharmacol. Dec. 1998;125(7):1437-44.

Sandborn, Strategies for targeting tumour necrosis factor in IBD.Best Pract Res Clin Gastroenterol. Feb. 2003;17(1):105-17. Review.

Sandouka et al., Carbon monoxide-releasing molecules (CO-RMs) modulate respiration in isolated mitochondria. Cell Mol Biol (Noisy-le-grand). Sep. 30, 2005;51(4):425-32.

Sandouka et al., Treatment with CO-RMs during cold storage improves renal function at reperfusion. Kidney Int. Jan. 2006;69(2):239-47.

Santucci et al., Pentoxifylline prevents indomethacin induced acute gastric mucosal damage in rats: role of tumour necrosis factor alpha. Gut. Jul. 1994;35(7):909-15.

Sarady et al., Carbon monoxide protection against endotoxic shock involves reciprocal effects on iNOS in the lung and liver. FASEB J. May 2004;18(7):854-6. Epub Mar. 4, 2004.

Sato et al., Carbon monoxide generated by heme oxygenase-1 suppresses the rejection of mouse-to-rat cardiac transplants. J Immunol. Mar. 15, 2001;166(6):4185-94.

Sawle et al., Carbon monoxide-releasing molecules (CO-RMs) attenuate the inflammatory response elicited by lipopolysaccharide in RAW264.7 murine macrophages. Br J Pharmacol. Jul. 2005;145(6):800-10.

Sawle et al., Homocysteine attenuates endothelial haem oxygenase-1 induction by nitric oxide (NO) and hypoxia. FEBS Lett. Nov. 23, 2001;508(3):403-6.

Schmidt et al., Manganese(I) and rhenium(I) pentacarbonyl(Trifluoromethanesulfatonato) complexes. In Inorganic Syntheses, Ed. Herbert D. Kaesz. vol. 26. Inorganic Syntheses, Inc. 1989:113-17.

Schubert, The action of carbon monoxide on iron and cobalt complexes of cysteine. Carbon Monixide on Iron and Cobalt Cysteine Complexes. 1933;55:4563-70.

Severin et al., Metal complexes of biologically important ligands. LXX. Synthesis, stereochemistry and reactions of ruthenium (II) and osmium (II) complexes with .alpha.-amino carboxylates. 1994; 127(4): 615-620. English abstract provided.

Shapiro, Carbonyl-trapping therapeutic strategies. Am J Ther. Sep. 1998;5(5):323-53. Review.

Shiohira et al., Protective effect of carbon monoxide donor compounds in endotoxin-induced acute renal failure. Am J Nephrol. 2007;27(5):441-6. Epub Jul. 12, 2007.

Silver et al., Mossbauer studies on protoprophyrin IX iron (II) solutions containing sulphur ligands and their carbonyl adducts. Inorg Chimica Acta. 1984;9:279-83.

Siow et al., Heme oxygenase-carbon monoxide signalling pathway in atherosclerosis: anti-atherogenic actions of bilirubin and carbon monoxide? Cardiovasc Res. Feb. 1999;41(2):385-94.

Sjöstrand, Endogenous formation of carbon monoxide in man under normal and pathological conditions. Scan J Clin Lab Invest. 1949;1:201-14.

Skattebøl et al., Synthesis of (±)-Lineatin, an aggregation pheromone component of *Trypodendron lineatum*. Acta Chem Scand B. 1985;39:291-304.

Soares et al., Expression of heme oxygenase-1 can determine cardiac xenograft survival. Nat Med. Sep. 1998;4(9):1073-7.

Song et al., Carbon monoxide inhibits human airway smooth muscle cell proliferation via mitogen-activated protein kinase pathway. Am J Respir Cell Mol Biol. Nov. 2002;27(5):603-10.

Song et al., Carbon monoxide inhibits T lymphocyte proliferation via caspase-dependent pathway. J Immunol. Jan. 15, 2004;172(2):1220-6.

Spector, Review: Oxidative stress and disease. J Ocul Pharmacol Ther. Apr. 2000;16(2):193-201. Review. Abstract only.

Srisook et al., CO from enhanced HO activity or from CORM-2 inhibits both O2- and NO production and downregulates HO-1 expression in LPS-stimulated macrophages. Biochem Pharmacol. Jan. 12, 2006;71(3):307-18. Epub Dec. 2, 2005.

Srisook et al., Role of NO In enhancing the expression of HO-1 in LPS-stimulated macrophages. Methods Enzymol. 2005;396:368-77.

Staal et al., The syntheses and coordination properties of M(CO)3X(DAB) (M= Mn, Re; X = Cl, Br, I; DAB= 1,4-diazabutadiene). J Organometal Chem. May 1, 1979:170(2):235-45. Abstract only.

Stagni et al., A water-soluble carbon monoxide-releasing molecule (CORM-3) lowers intraocular pressure in rabbits. Br J Ophthalmol. Feb. 2009;93(2):254-7. Epub Oct. 31, 2008.

Stanford et al., Carbon monoxide inhibits endothelin-1 release by human pulmonary artery smooth muscle cells. Eur J Pharmacol. Feb. 23, 2004;486(3):349-52.

Stanford et al., Heme oxygenase is expressed in human pulmonary artery smooth muscle where carbon monoxide has an anti-proliferative role. Eur J Pharmacol. Jul. 25, 2003;473(2-3):135-41.

Stec et al., Heme oxygenase-1 induction does not improve vascular relaxation in angiotensin II hypertensive mice. Am J Hypertens. Feb. 2008;21(2):189-93. Epub Jan. 3, 2008.

Stein et al., Administration of a CO-releasing molecule induces late preconditioning against myocardial infarction. J Mol Cell Cardiol. Jan. 2005;38(1):127-34. Epub Dec. 8, 2004.

Stone et al., Soluble guanylate cyclase from bovine lung: activation with nitric oxide and carbon monoxide and spectral characterization of the ferrous and ferric states. Biochemistry. May 10, 1994;33(18):5636-40.

Stone et al., Synergistic activation of soluble guanylate cyclase by YC-1 and carbon monoxide: implications for the role of cleavage of the iron-histidine bond during activation by nitric oxide. Chem Biol. May 1998;5(5):255-61.

Suematsu et al., Carbon monoxide: an endogenous modulator of sinusoidal tone in the perfused rat liver. J Clin Invest. Nov. 1995;96(5):2431-7.

Sun et al., Attenuation of leukocytes sequestration by carbon monoxide-releasing molecules: liberated carbon monoxide in the liver of thermally injured mice. J Burn Care Res. Jan.-Feb. 2007;28(1):173-81.

(56) References Cited

OTHER PUBLICATIONS

Sun et al., CO-releasing molecules (CORM-2)-liberated CO attenuates leukocytes infiltration in the renal tissue of thermally injured mice. Int J Biol Sci. Jun. 16, 2008;4(3):176-83.

Sun et al., Preconditioning of carbon monoxide releasing molecule-derived CO attenuates LPS-induced activation of HUVEC. Int J Biol Sci. Aug. 22, 2008;4(5):270-8.

Sun et al., Role of CO-releasing molecules liberated CO in attenuating leukocytes sequestration and inflammatory responses in the lung of thermally injured mice. J Surg Res. May 1, 2007;139(1):128-35. Epub Feb. 9, 2007.

Suzuki et al., Activated platelets in ulcerative colitis enhance the production of reactive oxygen species by polymorphonuclear leukocytes. Scand J Gastroenterol. Dec. 2001;36(12):1301-6. Abstract only.

Szakács-Schmidt et al., Iron (II) thiolates as reversible carbon monoxide carriers. Inorg Chimica Acta. 1992;198-200:401-5.

Szallasi et al., Dialdehyde sesquiterpenes and other terpenoids as vanilloids. Eur J Pharmacol. Aug. 28, 1998;356(1):81-9. Abstract only.

Taillé et al., Mitochondrial respiratory chain and NAD(P)H oxidase are targets for the antiproliferative effect of carbon monoxide in human airway smooth muscle. J Biol Chem. Jul. 8, 2005;280(27):25350-60. Epub Apr. 29, 2005.

Takács et al., Synthesis and molecular structure of carbonyl derivatives of Iron (II) thiolates containing nitrogen-donor ligands. Inorg Chemica Acta. 1989;166:39-46.

Tamaki, Role of second messenger gases in ischemia and reperfusion injury. Low Temp Med. 2001;27(1):1-5. English abstract provided.

Tayem et al., Protection against cisplatin-induced nephrotoxicity by a carbon monoxide-releasing molecule. Am J Physiol Renal Physiol. Apr. 2006;290(4):F789-94. Epub Nov. 15, 2005.

Tenhunen et al., Microsomal heme oxygenase. Characterization of the enzyme. J Biol Chem. Dec. 10, 1969;244(23):6388-94.

Tilg et al., Antitumour necrosis factor therapy in Crohn's disease. Expert Opin Biol Ther. Oct. 2002;2(7):715-21. Review. Abstract only.

Togane et al., Protective roles of endogenous carbon monoxide in neointimal development elicited by arterial injury. Am J Physiol Heart Circ Physiol. Feb. 2000;278(2):H623-32.

Tomita et al., Structure and reaction of bis(L-cysteinato)dicarbonyliron(II). Inorg Nucl Chem Lett. 1968;4:715-8.

Treichel et al., Synthesis and reactivity of bridging thiolato-manganese carbonyl complexes, Et4N[Mn2(μ-SR)3(CO)6]. J Organometall Chem. Sep. 10, 1985;292(3):385-93.

Tsuburai et al., The role of heme oxygenase in pulmonary circulation. Low Temp Med. 2001;27(1):28-35. English abstract provided.

Urban et al., Metal complexes of biologically important ligands, LXXXVII α-amino carboxylate complexes of palladium(II), iridium(III) and ruthenium(II) from chloro-bridged ortho-metallated metal compounds and [(OC)3Ru(Cl)(μ-Cl)]2. J Organomett Chem. 1996;517:191-200.

Urwyler et al., Positive allosteric modulation of native and recombinant gamma-aminobutyric acid(B) receptors by 2,6-Di-tert-butyl-4-(3-hydroxy-2,2-dimethyl-propyl)-phenol (CGP7930) and its aldehyde analog CGP13501. Mol Pharmacol. Nov. 2001;60(5):963-71.

Van Staveren et al., Spectroscopic Properties, Electrochemistry, and Reactivity of Mo0, MoI, and MoII Complexes with the [Mo(bpa)(CO)3] Unit [bpa = bis(2-picolyl)amine] and Their Application for the Labelling of Peptides. Eur J Inorg Chem. 2002;6:1518-29.

Vannacci et al., Evaluation of the effects of a novel carbon monoxide releasing molecule (CORM-3) in an in vitro model of cardiovascular inflammation. 1. Histamine in allergy, inflammation, tissue growth and repair. Inflamm Res. Apr. 2006;55 Suppl 1:S05-6.

Vannacci et al., The effect of a carbon monoxide-releasing molecule on the immunological activation of guinea-pig mast cells and human basophils. Inflamm Res. 2004;53 Suppl 1:S09-10.

Varadi et al., Beneficial effects of carbon monoxide-releasing molecules on post-ischemic myocardial recovery. Life Sci. Apr. 3, 2007;80(17):1619-26. Epub Feb. 2, 2007.

Vera et al., Protective effect of carbon monoxide-releasing compounds in ischemia-induced acute renal failure. J Am Soc Nephrol. Apr. 2005;16(4):950-8. Epub Feb. 23, 2005.

Verma et al., Carbon monoxide: a putative neural messenger. Science. Jan. 15, 1993;259(5093):381-4.

Verona et al., Regioselectivity in the nucleophilic functionalization of xanthene complexes of Mn(CO)3. J Organelle Chem. Nov. 1, 1996;524(1-2)71-80.

Viswanathamurthi et al., Synthesis, characterization and biocidal studies of ruthenium (II) carbonyl complexes containing tetradentate Schiff bases. Transition Metal Chemistry. 1999; 24(6):638-641.

Volti et al., Carbon monoxide signaling in promoting angiogenesis in human microvessel endothelial cells. Antiox Redox Signal. May 2005;7(5-6):704-10.

Vreman et al., Determination of carbon monoxide (CO) in rodent tissue: effect of heme administration and environmental CO exposure. Anal Biochem. Jun. 15, 2005;341(2):280-9. Abstract only.

Vulapalli et al., Cardioselective overexpression of HO-1 prevents I/R-induced cardiac dysfunction and apoptosis. Am J Physiol Heart Circ Physiol. Aug. 2002;283(2):H688-94.

Waibel et al., Stable one-step technetium-99m labeling of His-tagged recombinant proteins with a novel Tc(I)-carbonyl complex. Nat Biotechnol. Sep. 1999;17(9):897-901.

Wang et al., A correlation of the visible and Soret spectra of dioxygen- and carbon monoxide-heme complexes and five-coordinate heme complexes with the spectra of oxy-, carboxy-, and deoxyhemoglobins. Biochemistry. Oct. 30, 1979;18(22):4960-77.

Wang et al., Carbon monoxide-induced vasorelaxation and the underlying mechanisms. Br J Pharmacol. Jul. 1997;121(5):927-34.

Wang et al., Preconditioning limits mitochondrial Ca(2+) during ischemia in rat hearts: role of K(ATP) channels. Am J Physiol Heart Circ Physiol. May 2001;280(5):H2321-8.

Wang et al., The chemical modification of KCa channels by carbon monoxide in vascular smooth muscle cells. J Biol Chem. Mar. 28, 1997;272(13):8222-6.

Weigel et al., Inhibition of DNA replication in *Escherichia coli* by cyanide and carbon monoxide. J Biol Chem. Nov. 10, 1975;250(21):8536-42.

Willis et al., Heme oxygenase: a novel target for the modulation of the inflammatory response. Nat Med. Jan. 1996;2(1):87-90.

Wu et al., Carbon monoxide: endogenous production, physiological functions, and pharmacological applications. Pharmacol Rev. Dec. 2005;57(4):585-630. Review.

Wu et al., Different mechanisms underlying the stimulation of K(Ca) channels by nitric oxide and carbon monoxide. J Clin Invest. Sep. 2002;110(5):691-700.

Xi et al., Carbon monoxide activates KCa channels in newborn arteriole smooth muscle cells by increasing apparent Ca2+ sensitivity of alpha-subunits. Am J Physiol Heart Circ Physiol. Feb. 2004;286(2):H610-8. Epub Oct. 16, 2003.

Xu et al., A facile method for synthesis of (R)-(-)- and (S)-(+)-homocitric acid lactones and related α-hydroxy dicarboxylic acids from d- or l-malic acid. Tetrahedron Lett. May 30, 2005;46(22):3815-18. Abstract only.

Yachie et al., Oxidative stress causes enhanced endothelial cell injury in human heme oxygenase-1 deficiency. J Clin Invest. Jan. 1999;103(1):129-35.

Yan et al., Cytotoxicity of rhenium(I) alkoxo and hydroxo carbonyl complexes in murine and human tumor cells. Pharmazie. Apr. 2000;55(4):307-13.

Yet et al., Cardiac-specific expression of heme oxygenase-1 protects against ischemia and reperfusion injury in transgenic mice. Circ Res. Jul. 20, 2001;89(2):168-73.

(56) References Cited

OTHER PUBLICATIONS

Yet et al., Induction of heme oxygenase-1 expression in vascular smooth muscle cells. A link to endotoxic shock. J Biol Chem. Feb. 14, 1997;272(7):4295-301.

Zhang et al., Carbon monoxide inhibition of apoptosis during ischemia-reperfusion lung injury is dependent on the p38 mitogen-activated protein kinase pathway and involves caspase 3. J Biol Chem. Jan. 10, 2003;278(2):1248-58. Epub Oct. 23, 2002.

Zimmerman et al., Cerebroprotective effects of the CO-releasing molecule CORM-A1 against seizure-induced neonatal vascular injury. Am J Physiol Heart Circ Physiol. Oct. 2007;293:H2501-H2507.

Zuckerbraun et al., Carbon monoxide protects against the development of experimental necrotizing enterocolitis. Am J Physiol Gastrointest Liver Physiol. Sep. 2005;289(3):G607-13. Epub May 12, 2005.

Zuckerbraun et al., Carbon monoxide reverses established pulmonary hypertension. J Exp Med. Sep. 4, 2006;203(9):2109-19. Epub Aug. 14, 2006.

* cited by examiner

METHOD FOR TREATING A MAMMAL BY ADMINISTRATION OF A COMPOUND HAVING THE ABILITY TO RELEASE CO

CROSS-REFERENCE TO RELATED APPLICATIONS

This application is a divisional application of U.S. application Ser. No. 11/288,670, filed Nov. 29, 2005, which is a divisional application of U.S. application Ser. No. 10/356,738 (now U.S. Pat. No. 7,011,854), filed Feb. 3, 2003, which is based on and claims the benefit of U.S. Provisional Application No. 60/353,233, filed Feb. 4, 2002. The entire disclosure of these applications are relied upon and incorporated by reference herein.

BACKGROUND OF THE INVENTION

The history of analgesic and anti-inflammatory medicines started with the use of decocted salicylate-containing plants by ancient Greek and Roman physicians. Willow bark was already used 300 BC for treating fever and pain. Sodium salicylate was introduced in 1875 as an antipyretic. At Bayer in Germany the less corrosive acetylsalicylic acid was synthesized and introduced into medicine in 1899 under the name of aspirin.

The impressive anti-inflammatory, analgesic and antipyretic effects of aspirin prompted researchers to develop a large number of related compounds most of which are organic acids. These compounds, referred to as aspirin-like drugs or nonsteroidal anti-inflammatory drugs (NSAIDs) are a heterogeneous group of substances which have no uniform chemical properties but share the same therapeutic effects as well as unwanted side effects. In 1971 Vane and colleagues have shown that aspirin and other NSAIDs inhibited the synthesis of prostaglandins. Prostaglandins serve many diverse functions throughout the body, with important roles in blood clotting, ovulation, initiation of labor, bone metabolism, nerve growth and development, wound healing, kidney function, blood vessel tone, and immune response (DuBois R. N. et al FASEB J. 1998, 12, 1063). Prostaglandins are produced locally in many different tissue types and have different local actions. PGE2 is generally thought to be the most important pro-inflammatory prostaglandin mediating tissue swelling, fever and hyperalgesia (heightened pain sensitivity). However, other prostanoids may be equally important. Prostacyclin (PGI2), for example, is likely to play an important role in the development of inflammatory pain (K. R. Bley, J. C. Hunter, R. M. Eglen and J. A. M. Smith; 1998, Trends in Pharmacological Science 19, 141-147). Another prostanoid, thromboxane, is produced by platelets and plays a crucial role in thrombotic events. The first enzyme in the prostaglandin synthetic pathway is fatty acid cyclooxygenase, which occurs in two forms, COX-1 and COX-2. COX-1 is constitutively expressed in many cells and tissues such as stomach, kidney and platelets, while COX-2 is induced at sites of injury by exogenous and endogenous inflammatory mediators. Aspirin acetylates serine residues in COX-1 and COX-2 thus resulting in irreversible inhibition of these enzymes. Other NSAIDs are reversible, competitive inhibitors of cyclooxygenases.

Because aspirin and other NSAIDs are organic acids and have a high capacity to bind to proteins, they accumulate in inflamed tissues, the GI mucosa, the renal cortex, the blood and in the bone marrow. These facts are well known and can be found in textbooks of Pharmacology such as Goodmann and Gilman's Pharmacological Basis Of Therapeutics, McGraw-Hill, New York.

Aspirin is rapidly deacetylated by the liver. However, COX-1 in platelets can be inhibited by low doses of aspirin in the portal circulation, thereby sparing COX-1 in endothelial cells and prostacylin synthesis (Benett 2001). NSAIDs are the most widely used drugs in the world; about 70 million people each day take prescribed NSAIDs, and about 200 million people each day take over-the-counter NSAIDs (Smith T. G. Rheum. Dis. Clin. North Am. 1998, 24, 501-523). In the United States 80 billion aspirin tablets are consumed annually (Flieger K. FDA Consum. January-February 1994) and about 50 million people spend $5-10 billion on NSAIDs each year (DuBois R. N. et al FASEB J. 1998, 12,1063). Since the determination of these figures in 1999, it is most likely that the use of NSAIDs has further increased. Population studies have shown that 10-20% of all people who are 65 years or older are either currently receiving or have recently received a prescription for a nonsteroidal anti-inflammatory drug. During the next 20 years the number of people over 65 is expected to increase from 380 million to 600 million.

The frequent use of NSAIDs is based on the fact that it has many indications including mild headache, menstrual pain, fever, chronic polyarthritis, psoriatic arthritis, ankylosing spondylitis, osteoarthritis, gout, inflammatory soft tissue rheumatis, low back pain, postoperative and post-traumatic inflammation, thrombophlebitis and vasculitis (Juergen Steinmeyer, 2000, Arthritis Research 2, 379-385). In addition to the traditional use for the above indications, NSAIDs have been shown to be effective in the prevention of vascular disorders. Aspirin is the most widely used inhibitor of platelet function and is the standard against which other agents are judged. In the Antiplatelet Trialist Collaboration (46 trials with patients with acute myocardial infarction, prior myocardial infarction, unstable angina, stroke, or transient ischemic attack, aspirin reduced the long term risk of recurrent infarction, stroke, or death from a vascular cause by 25%. Aspirin acetylates COX-1 not only in platelets, but also in endothelial cells thereby preventing the synthesis of prostacyclin, a potent vasodilatator and platelet inhibitor. Despite the inhibition of prostacyclin, aspirin has a net anti-platelet effect by inhibiting thromboxane A2 synthesis in platelets (Benett 2001).

Not all biological effects of NSAIDs are related to the inhibition of cyclooxygenases. Other potential targets include nuclear receptors such as peroxisome proliferator activated receptor gamma and delta (PPAR γ and δ), kinases such as Ikb kinase (IKKβ), and certain phosphodiesterases such as PDE5 and 2. Interactions of NSAIDs with such target depends on the structure and dose of the compound, and may have beneficial or adverse consequences.

NSAIDs are generally well tolerated; however, adverse reactions do occur in a small but important percentage of patients. Because of the very extensive use of NSAIDs this results in substantial morbidity and mortality. The most serious side effect of aspirin and related NSAIDs are gastrointestinal disorders, in particular the induction of gastroduodenal ulcers. Long term administration of aspirin also leads to a small increase in the number of hemorrhagic strokes. There is a dose dependent relationship to both complications. They can be minimized, but not eliminated, by administering the lowest effective dose of aspirin. The annual number of hospitalizations in the United States for serious gastrointestinal complications of NSAID use is at least 100,000 and the annual direct costs of such complications exceed U.S. $2 billion. The mortality rate among patients who are hospitalized for NSAID induced upper gastrointestinal bleeding is about 5 to 10% (for references to original articles see Wolke M. M., Lichtenstein D. R. and G. Singh, 1999; The New England Journal of Medicine 340, 1888-1899).

Extensive efforts have been made to prevent the adverse effects of NSAIDs. One strategy which has proven to be effective is to supplement NSAIDs medication with protective prostaglandin derivatives, such as misoprostol, or with a proton pump inhibitor, such as ranitidine. Another strategy is to modify NSAIDs themselves either to make them more selective or to add protective moieties. Safer NSAIDs have been developed, which selectively inhibit only the inducible cyclooxygenase, COX-2. The increased safety profile of selective COX-2 inhibitors is thought to be due to the fact that prostaglandins generated by COX-2 at the sites of injury cause tissue swelling, pain and inflammation, while those generated by COX-1 in the mucosa and by platelets have protective functions. Two selective COX-2 inhibitors, celcoxib (Celebrex®) and rofecoxib (Vioxx®) have become available and several related compounds are in early clinical development. Celecoxib and rofecoxib maintain selectivity for COX-2 even at high doses. It has been demonstrated in several clinical trials that these novel NSAIDs do cause less gastrointestinal complications than nonselective COX inhibitors.

Recent studies have shown that selective COX-2 inhibitors might open up a wide spectrum of new indications for NSAIDs. The degeneration of large areas of the brain in Alzheimer's disease is supposed to occur with the involvement of COX-2. Selective COX-2 inhibitors might also be directed towards the therapy of colorectal carcinomas. COX-2 expression is also increased in gastric and breast carcinomas, suggesting that selective COX-2 inhibitors might also be therapeutically useful for treating those tumours. Recently the US FDA approved the selective COX-2 inhibitor celecoxib for the treatment of the rare genetic disorder called familial adenomatous polyposis. Animal experiments have shown that COX-2 inhibitors inhibit angiogenesis and tumour growth in a dose dependent manner. COX-2 is expressed in the newly created blood vessels (especially in the endothelial cells) needed for tumour growth.

The advent of COX-2 selective compounds has motivated scientists to revisit the physiological and pathological role of the two known cyclooxygenase isozymes. These studies have revealed several potential disadvantages of cyclooxygenase inhibitors in general, and of selective COX-2 inhibitors in particular. While selective COX-2 inhibitors are effective in preventing colon cancer and possibly Alzheimers disease (Tocco G., Freire-Moar J. and Schreiber S. S.; 1997, Exp. Neurol 144, 339), they do not provide the prophylactic benefits of aspirin in vascular disease, which is largely, if not exclusively based on the reduction of COX-1 mediated thromboxane A2 synthesis in platelets. COX-2 was shown to have not only pro- but also anti-inflammatory properties (reviewed by P. R Colville-Nash and D. W. Gilroy; 2001, BioDrugs 15,1-9). In a crageenan induced pleurisy model in rats COX-2 first generated PGE2, which increased the transactivation function of NFkB and thereby upregulated the expression of many inflammatory mediators. At a later time point a shift occurred in which, by unknown mechanisms, PGE2 production was down regulated, while the production of cyclopentenone prostaglandins was increased. The "late" prostaglandins, which include PGD2 and its derivatives, in particular PGJ2, inhibit inflammation, at least in part by inhibiting NFkB signal transduction (A. Rossi, P. Kapahi, G. Natoli, T. Takahashi, Y. Chen, M. Karin and M. G. Santoro; 2000, Nature 403,103-108). These findings indicate that cycloxygenase inhibitors may delay the resolution of inflammation (see B. Poligone and A. S. Baldwin; 2001, The Journal of Biological Chemistry 276, 38658-64). Indeed cyclooxygenase inhibitors have been shown to delay gastric ulcer healing in mice (H. Mizunonet; 1997, Gastroenterology 112, 387-397) and to exacerbate induced colitis in rats (A. Schmassmann, B. M. Peskar, C. Stettler, et al; 1998, Br. J. Pharmacology 123, 795-804; M. N. Ajuebor, A. Singh, and J. L. Wallace; 2000, Am J. Physiol. Gastrointest Liver Physiol 279, G238-44). In some patients treated with selective COX-2 inhibitors ulcers have progressed further to perforation.

A more recent study suggests that COX-2 mediated prostaglandin production is required for the generation of TGFβ producing regulatory T cells that mediate oral tolerance to dietary antigens (for references see O. Morteau; 1999, Nature Medicine 5, 867-8). Sugawa and colleagues pointed out that COX-2 inhibitors may increase the production of leukotrienes, such as leukotriene B4 (LTB4), which is one of the most potent chemotactic/inflammatory factors (K. Sugawa, T. Uz, V. Kumar and H. Manev; 2000, Jpn J Pharmacol 82, 85). In chronically inflamed pulmonary tissue, NSAIDs lead to an increased production of leukotrienes and in this way to asthma-like reactions due to the inhibition of prostaglandin synthesis. COX-2 has also been reported to be involved in the regulation of the renin-angiotensin system, and to possess vasoactive anti-atherogenic properties (G. Dannhardt and W. Kiefer; 2001, European Journal of Medicinal Chemistry 36,109-126). Based on these findings, COX-2 inhibitors might be expected to delay the resolution of inflammatory lesions and to exacerbate hypertension and atherocleosis. Thus, selective COX-2 inhibition is likely not to be the final triumph of the search for improved version of sodium salicylate, which began more than 100 years ago.

Another strategy to reduce the side effects of aspirin and aspirin-like drugs has been the attachment of NSAIDs with protective compounds. At least part of the toxicity of NSAIDs has been ascribed to their ability to bind to zwitterionic phospholipids, which provide the mucus gel layer with non-wettable properties. Preassociating NSAIDs with exogenous zwitterionic phospholipids prevented them from increasing the wettability of the mucus gel layer and protected rats against the injurious gastrointestinal side effects of these drugs, while enhancing their lipid permeability, anti-pyretic and anti-inflammatory activity (L. M. Lichtenberg, Z. M. Wang, J. J. Romero, C. Ulloa, J. C. Rerez, M. N. Giraud and J. C. Baretto, 1995, Nat Medicine 1, 154).

Another approach, which is currently in clinical testing, utilizes NSAIDs that are covalently derivatized with a nitric oxide (NO) releasing moiety (NO-NSAIDs). This strategy, which has been described in a series of patents (U.S. Pat. Nos. 5,621,100; 5,700,947; 5,861,426; 6,040,341; 6,218,417 B1; 6,218,417 B1; and 6,242,432) is based on the observation, that, NO has cytoprotective properties. In particular in the stomach, NO exhibits many of the same actions as prostaglandins, such as stimulation of mucus secretion and maintenance of mucosal blood flow. Indeed, NO-NSAIDs did not cause any gastrointestinal injuries in animals, and exhibited anti-inflammatory and analgesic effects, which exceeded those of the parent compounds (for references see P. del Soldato, R. Sorrentino and A. Pinto; 1999, Trends I PharmacologicalScience 20, 319). The NO release from these compounds is a metabolic rather than a spontaneous process. The anti-inflammatory effects of these compounds are thought to be due in part to the inhibition of cyclooxygenases, and in part to the nitrosation and inactivation of caspase 1, an enzyme, that is required for the generation of at least two inflammation promoting cytokines, interleukin 1 and interleukin 18 (S. Fiorucci; 2001, Trends in Immunology 22, 232-235). Clinical studies must be undertaken to compare NO-NSAIDs and their parent drugs with regard to safety profile and therapeutic efficacy.

In contrast to COX-2 inhibitors nitro-aspirin is expected to retain or even surmount the prophylactic effect of aspirin in cardiovascular disease. One of the nitro-aspirin compounds, referred to as NC4016, inhibited arachidonic acid-stimulated aggregation of platelets at a concentration of 100 μM, whereas aspirin induced the same effect at 10 μM. However NC4016 was more efficient than aspirin in inhibiting platelet aggregation and adhesion induced by thrombin. The anti-thrombotic effect of NC4016 appears to be due at least in part to the release of NO, which results in increased cGMP levels in platelets, as well as to the inhibition of prostanoid synthesis.

Many diverse effects have been ascribed to endogenously produced NO and to therapeutically administered NO or NO donors. These include regulation of blood flow, maintenance of vascular tone, control of platelet aggregation, and various roles in the central and peripheral nervous system. The phenomenology described in the literature is rather complex. NO has been reported to have either pro- or anti-inflammatory effects (H. Kolb and V. Kolb-Bachofen; 1998, Immunology Today 19, 556) and pro- or anti-atherogenic effects (R. P. Patel, A. Levonen, J. H. Crawford, and V. M. Darley-smar; 2000, Cardiovascular Research 47, 465-74). Therefore, it is difficult to predict the long term effects of compounds, which exhibit sustained NO release.

There exists a need in the art for methods for preventing and/or treating diseases, for example, inflammatory diseases. In addition, there is a need for compounds and pharmaceutical compositions for preventing and/or treating diseases, for example, inflammatory diseases.

SUMMARY OF THE INVENTION

This invention aids in fulfilling these needs in the art by providing a method for preventing and/or treating a disease in a mammal, wherein said method comprises a step of administering to said mammal a compound having the capability to release carbon monoxide (CO) in vivo. The compound has the ability to release CO in vivo in a target site, for example in an inflammatory or pre-inflammatory site.

In preferred embodiments, the method is used for preventing and/or treating inflammatory disease or disease with a strong inflammatory component, asthma, injury, infarction, circulatory disease.

As used herein, a target site means a site where a therapeutic effect is expected by use of a compound of the invention. Such therapeutic effect can be obtained at least partly by means of the released CO as active principle.

Thus, a compound for use in the method according to the invention is characterized in that it comprises at least one CO-releasing moiety.

As used herein, a CO-releasing moiety means a moiety having the ability to release carbon monoxide in vivo. Examples of such moieties are moieties containing CO and include a moiety that comprises of CO. Other examples of CO-releasing moieties are moieties 'capable of generating CO. CO can be released in certain conditions (e.g. oxidative conditions of a targeted pre-inflammatory or inflammatory site.)

In a particular embodiment, the CO-releasing moiety is linked to a second moiety. This second moiety is, for example, a drug carrier and/or a therapeutic agent such as, for instance, an anti-inflammatory agent. It may be selected depending on its known capacity to target the site/tissue in which a therapeutic effect is expected. For example, an anti-inflammatory agent can be selected for its known capacity to accumulate in an inflammatory lesion.

Anti-inflammatory drugs, which accumulate in inflamed tissues, include aspirin, indomethacin, nimesulide, vioxx, celecoxib and other nonsteroidal anti-inflammatory drugs that are organic acids.

The CO releasing moiety may also be targeted to bones by using biphosphonates as carriers.

The CO releasing moiety may also be targeted to any particular tissue or cell type by using proteins as carrier. Carrier proteins include but are not limited to antibodies which are specific for a cell surface protein or a component of the extracellular matrix.

In a preferred embodiment of the invention, the compound having the ability to release carbon monoxide in vivo is a compound from one of the following classes:

Class 1—CO containing organometallic complex. Such a compound can be dissolved in physiologically compatible support.

Class 2—CO containing organometallic complex linked to at least another pharmacologically important molecule. For example, said pharmacologically important molecule is a carrier, a drug (e.g., an anti-inflammatory agent). Furthermore, the CO containing organometallic complex and the at least other pharmacologically important molecule are optionally linked by means of an appropriate spacer.

Class 3—Supramolecule aggregates made of CO containing organometallic complexes optionally encapsulated e.g. in a cyclodextrin host and/or another appropriate inorganic or organic support.

Class 4—CO containing inorganic complex bearing ligands, e.g., polidentate ligands, containing N and/or S donors that function as reversible CO carriers.

Class 5—CO containing inorganic complex bearing ligands, e.g. polidentate ligands, containing N and/or S donors that function as reversible CO carriers, linked to at least another pharmacologically important molecule. For example, the pharmacologically important molecule is a carrier, a drug, (e.g. an anti-inflammatory agent). Furthermore, the CO containing organometallic complex and the at least other pharmacologically important molecule are optionally linked by means of an appropriate spacer.

Class 6—Organic substances that release CO either by an enzymatic process or by decarbonylation. Such a compound can be dissolved in physiologically compatible supports.

Class 7—Organic substances that release CO either by an enzymatic process or by decarbonylation, e.g., dichloromethane optionally encapsulated either in cyclodextrin hosts and/or other appropriate inorganic or organic supports.

This invention also provides a pharmaceutical composition, which comprises a compound of the invention having the ability to release carbon monoxide in vivo. In a preferred embodiment, the pharmaceutical composition can be used for preventing and/or treating inflammatory diseases. In one embodiment of the invention, the inflammatory disease is a chronic inflammatory disease, such as rheumatoid arthritis. In another embodiment, the pharmaceutical composition can be used for preventing and/or treating asthma injury, infarction, circulatory disease.

In one embodiment, the method for preventing and/or treating a disease in a mammal according to the invention comprises a step of administering to said mammal a pharmaceutical composition of the invention. The method comprises administering a pharmaceutical composition of the invention to a mammal, such as humans, and various animal species, including cats, dogs, cows, pigs, horses, sheep, and goats. In a preferred embodiment, this invention provides a method for preventing and/or treating inflammatory disease, e.g. chronic inflammatory disease, such as rheumatoid arthritis.

DETAILED DESCRIPTION OF THE INVENTION

The present invention describes several classes of compounds designed to release carbon monoxide (CO) in vivo. This invention is based on recent evidence that carbon monoxide is an endogenous mediator that has anti-inflammatory and anti-thrombotic properties. Carbon monoxide has long been known to inhibit human platelet aggregation (Brune and Ullrich, 1987, Mol Pharmacol 32, 497). Within the past decade observations have accumulated which suggest that CO is an endogenous mediator of a variety of physiological processes. CO was shown to cause vasodilation (Sammut et al, 1998, British Journal of Pharmacology 125,1437), to support graft survival in allogeneic or xenogeneic hosts (Soares et al 1998, Nature Medicine 4,1073), and to ameliorate inflammatory reactions (Otterbein et al, 2000, Nature Medicine 6, 422). Carbon monoxide (CO) is a diatomic, diffusible, colorless gas. The principal advantage of CO as a mediator of therapeutic and preventive measures is its stability and limited reactivity. The biological effects of CO do not depend on the formation of intermediary, more stable mediators. The potential of CO-releasing compounds in therapeutic and prophylactic medicine will become apparent from the following brief review of the known facts about CO and of its role in physiological and pathological processes.

In the body, generation of CO requires heme oxygenase. The enzyme was initially found to be involved in the degradation of heme in aging red blood cells. It carries out the oxidation of the heme molecule (Fe-protoporphyrin IX) in concert with oxygen and NADPH-cytochrome P450 reductase. Heme oxygenase is induced by heme, enabling it to respond to hemolysis or tissue destruction, which releases heme from hemoglobin of erythrocytes and from mitochondrial enzymes of nucleated cells, respectively. The products of the catalytic degradation of heme are CO, ferric iron, and bilirubin, which is rapidly converted into biliverdin. Thus, heme oxygenase serves catabolic and anabolic functions within cells. In its catabolic function it downregulates cellular heme and hemoprotein levels and thereby inactivates the most effective catalyst for the formation of free radicals, the heme molecule. In its anabolic role, heme oxygenase produces bile pigments, CO, and iron, all of which are biologically active. The bile pigments bilirubin and biliverdin function as antioxidants. Iron regulates expression of various genes, including that of HO-1 itself, as well as transferin receptors, ferritin, and NO synthase. Most important with respect to the present invention is the third product, carbon monoxide (CO), which acts as a signal transducer.

Heme is not only the only known source of CO in the body, it is also the only known target. In physiological systems, heme is bound to certain proteins, which bind oxygen at the site of the iron atom or function as components of the membrane bound electron transport system. Cellular respiration, energy generation, and chemical oxidations are dependent on these heme proteins. Heme proteins include hemoglobin, myoglobin, catalase, cytochrome b5, all cytochrome P450s, tryptophan pyrrolase, NO synthetase isozymes, and soluble guanylate cyciase (sGC). The latter enzyme is the best characterized mediator of the biological effects of NO and CO. Binding of NO to the prosthetic heme group of sGC activates the enzyme to generate guanosine 3',5'-monophosphate (cyclic GMP or cGMP). cGMP in turn activates one or more protein kinases, at least some of which phosphorylate proteins that are involved in Ca++ flux. CO is a much weaker activator of purified sGC in vitro than NO. However, attachment of a small molecular weight compound referred to as YC-1, and possibly of an as yet unknown, endogenous cofactor, dramatically increases the sensitivity of the enzyme to its activation by CO. Cyclic GMP is degraded and thus inactivated by several phosphodiesterases, which exhibit a tissue specific expression pattern. Thus NO and CO mediated signal transduction is under the control of NO and CO generating enzymes, as well as cGMP inactivating phosphodiesterases. In the context of the present invention it is important to note that the cGMP mediated effects of CO releasing compounds can be augmented by attaching such compounds to known phosphodiesterase inhibitors (see below). Because of the tissue specific expression of phosphodiesterases (PDEs), this strategy allows to target the effect of released CO to particular tissues.

PDE3 and PDE4 isozymes, for example, are expressed in the airway, vascular smooth muscle cells, heart, liver, endothelial cells, monocytes and T cells. PDE4 isozymes are in addition expressed in the brain, platelets, neutrophils, eosinophils and mast cells (Conti M. and Jin L; 1999, Progr Nucleic Acid Res. Mol. Biol. 63, 1-38) and PDE7 is inducible in T cells (Li L, Yee C, and Beavo J. A.; 1999, Science 283, 848-851). The effect of CO may be augmented in specific cell types by the concomitant inhibition of one or a set of PDEs. A particularly strong augmenting effect can be expected if the CO-releasing moiety is attached to inhibitors of cGMP selective PDEs.

Many of the biological effects of CO have been revealed through studies of the heme oxygenases (HOs). Three isoforms of heme oxygenases are known, HO-1, HO-2, and HO-3. HO-1 (also known as heat shock protein 32 or HsP32) is induced not only by heme, but by a large variety of exogenous and endogenous agents, which induce inflammatory responses or which are present in pathological conditions with a strong inflammatory component, such as atherosclerosis or Alzheimer's disease. HO-1 deficient mice develop an anemia associated with low serum iron levels. Iron accumulates in particular in the kidney and the liver leading to oxidative damage, tissue injury, and chronic inflammation (K. D. Poss and S. Tonegawa; 1997, Proc. Natl. Acad. Sci. USA 94, 10919-10924).

HO-2 is constitutively expressed in all cell types, and its expression is not affected by the stimuli, which induce HO-1. The only known regulator of HO-2 yet identified is adrenal glucocorticoid. HO-2 is a hemoprotein with two putative heme regulatory motifs (HRMs) and one site being the 24-residue conserved "heme pocket" catalytic domain. Heme, in particular in its protein bound form, activates molecular oxygen and forms reactive oxygen radicals. Thus, HO-2 may function as a heme sensor and as such serve as a regulator of heme-responsive genes, including the gene that encodes HO-1. The oxygen radical generating function of HO-2 is thought to have a physiological role in sperm cells, which depend on hydroxyl radicals for function. HO-2 is expressed in the central and peripheral nervous system at various sites. The deletion of the HO-2 gene revealed an important function of HO-2 and its product, CO, in nonadrenergic, noncholinergic (NANC) transmission in myenteric ganglia. Studies with HO inhibitors depleted cGMP levels in olfactory neurons suggested a neurotransmitter function of CO in these cells (reviewed by D. E. Baranano and S. H. Snyder; 2001, Proc. Natl. Acad. Sci. USA 98, 10996-11002).

HO-3 transcripts are found in the spleen, liver, thymus, prostate, heart, kidney, brain and testis. This isoform has only negligible enzymatic activity. It has two putative heme binding sites and is thought to have a regulatory role in heme dependent, cellular processes.

Within the last 5 years many studies have demonstrated protective effects of CO in a variety of disease models in animals. Lipopolysaccharide (LPS), a constituent of the gram-negative bacterial cell wall, is a potent inducer of inflammation. L. Otterbein and colleagues have shown in vitro using murine macrophages, and in vivo in mice, that CO at low concentrations inhibited the LPS induced production of two pro-inflammatory cytokines, tumor necrosis factor- a and interleukin 1-β, but increased the production of the anti-inflammatory cytokine interleukin 10 (L. E. Otterbein, F. H. Bach, J. Alam, M. Soares, H. T. Lu, M. Wysk, R. J. Davis, R. A. Flavell and A. M. K. Choi; 2000, Nature Medicine 6, 422-428).

Fujita and colleagues studied the effects of CO in a model of lung injury induced by ischemia/reperfusion in mice. HO-1 deficient mice died from ischemic lung injury, but could be rescued by inhaled CO. The beneficial effect of CO was shown to be due to the reduction of platelet adhesion, an increase in the microcirculatory blood flow and the inhibition of expression of plasminogen activator inhibitor 1 (PAI-1), thereby enhancing fibrinolysis and reducing intravascular thrombosis. It should be noted that inhalation of only 65 p.p.m. NO was as effective in reducing mortality as inhalation of 500-1000 p.p.m. CO. (T. Fujita, K. Toda, A. Karimova, S-F. Yan, Y. Naka, S-F. Yet and D. J. Pinsky; 2001, Nature Medicine 7, 598-604).

Using a similar model in rats, Otterbein and colleagues demonstrated that CO inhalation reduced neutrophil infiltration and lung injury and increased survival of the animals. The therapeutic effects were achieved with CO concentrations far less than the toxic concentrations and even less than the concentrations used in human pulmonary function tests. (L. E. Otterbein, L. L. Mantell and A. M. K. Choi; 1999, Lung Cell. Mol. Physiol. 20, L688-L694). Already in 1987, B. Brune and V. Ullrich showed that CO inhibits platelet aggregation (B. Brune and V. Ullrich; 1987, Mol. Pharmacol. 32, 497-504). A study by Steiner and colleagues indicates that CO has an anti-hyperalgesic effect in inflamed paws of rats (A. A. Steiner, L. G. Branco, F. Q. Cunha, and S. H. Ferreira; 2000, Br. J. Pharmacol. 132, 1673-1682). Several recent studies demonstrate striking effects of HO-1 and CO on blood vessels, endothelial cells, and vascular smooth muscle cells. Duckers and colleagues using gene transfer and gene knock out techniques demonstrated a protective role of HO-1 expression in arterial wound repair. HO-1 effects mediated fully or in part by its product CO included inhibition of vasoconstriction and inhibition of smooth muscle cell proliferation (H. J. Duckers, M. Boehm, A. L. True, S-F Yet, H. San, J. L Park, R. C. Webb, M-E. Lee, G. J. Nabel and E. G. Nabel; 2001, Nature Medicine 7, 693-698). Togane and colleagues demonstrated that CO inhibits vascular smooth muscle cell proliferation and neointimal formation after balloon injury (T Y. Togane, T. Morita, M. Suematsu, J. I. Yamazaki, and S. Katayama; 2000, Am. J. Physiol. Heart Circ. Physiol. 278, H623-632). Several groups demonstrated that low concentrations of CO prevent endothelial cell death (see for example S. Brouard, L. E. Otterbein, F. Anrather, E. Tobiasch, F. H. Bach, A. M. K. Choi, and M. P. Soares; 2000, J. Exp. Med. 192, 1015-1025). M. Soares and colleagues also have shown that expression of HO-1 is essential for the survival of xenotransplants. Mouse hearts transplanted to rats survive long term if the recipients are treated with cobra venom factor and cyclosporin. Inhibition of hemoxygenase by tin protoporphyrin caused acute rejection in 3-7 days. The rejection was associated with platelet aggregation, thrombosis of coronary arterioles, myocardial infarction, and apoptosis of endothelial cells and cardiac myocytes. These injuries to the graft and its rejection were prevented by exposing the recipients to air containing 400 p.p.m. CO (K. Sato, J. Balla, L. Otterbein et al; 2001, J. Immunology 166,4185-4194).

The above-described findings suggest that hemoxygenases are potential targets for drugs that are useful in a variety of pathological conditions. Drug candidates include compounds that induce or inhibit the expression of HO-1, and compounds that inhibit or augment the catalytic activity of hemoxygenases. Inhibitors of HO-1 expression or of its enzymatic activity may be useful for treating pathological conditions that are mediated at least in part by excessive amounts of either one of the three hemoxygenase products, CO, bilirubin, and iron. Endotoxin shock is induced by bacterial cell wall derived lipopolysaccharides (LPS, also known as endotoxin). LPS induced HO-1 generates CO, which may contribute to the reduction in vascular tone during sepsis. U.S. Pat. No. 5,888, 982 describes strategies that aim to inhibit sepsis induced hypotension by inhibitors of HO-1 transcription, such as antisense oligonucleotides, and/or by inhibitors of the enzymatic activity of hemoxygenases. Hemoxygenase inhibitors, which block the binding of heme to hemeoxygenases may also be used to reduce heme catabolism thereby preventing the release of iron and bilirubin, and increasing the rate at which heme and iron are excreted into the intestine. Such compounds including tin mesoporphyrin (SnMP, U.S. Pat. No. 4,657,902) and diidodeuteroporphyrin (Sn12DP, U.S. Pat. No. 4,699,903) may be used for treating neonatal hyperbilirubinemia and other conditions associated with toxic bilirubin levels such as various forms of anemias and liver diseases. Hemeoxygenase inhibitors have also been proposed for the treatment of immunesuppressed patients, for example for treatment of AIDS patients (U.S. Pat. No. 6,066,333). Compounds that induce the expression and/or augment the enzymatic activity of hemoxygenases are useful for treating chronic inflammatory diseases, asthma, injury, atherosclerosis and infarction. Hemoxygenase inducers described in U.S. Pat. No. 6,066,333 include prostaglandins of the A series, vitamin B12, hemin, hemin derivatives, and compounds that decrease nitric oxide synthesis. Heme-bearing microparticles have been proposed to be used for the targeted delivery of drugs to heme receptor bearing cells in the liver for the treatment of viral hepatitis and hepatoma (U.S. Pat. No. 5,891, 689). Such compounds may induce HO-1 expression. Therapeutic HO-1 expression could also be achieved by gene transfer as described in U.S. Pat. No. 6,203,991. The above described strategies aiming to augment HO-1 activity are complicated by the fact that hemoxygenases not only generate CO, but also two potentially toxic compounds, bilirubin and iron.

Alternatively, CO could be administered as a gas, for example by a pneumatic system as described in U.S. Pat. No. 5,664,563 or by local applications, for example, to stented coronary arteries or to organs before transplantation. Gaseous CO has been evaluated as a therapeutic agent long before its endogenous mediator function has been recognized. More than 25 years ago Beutler administered CO at a concentration of 1000-2000 p.p.m. to two sickle cell disease patients. In both patients, significant anti-sickling effects and prolongation of red cell survival was observed. Beutler did not recommend CO as a treatment for sickle cell disease, but suggested that further trials should be conducted under carefully controlled conditions (E. Beutler; 1975, Blood 46, 253-259). In a more recent comment on the beneficial effects of CO inhalation in a lung ischemia/reperfusion model in rodents, Thiemermann was not in favor of CO inhalation therapy of patients, as he believes that the dangers of CO inhalation outweigh the benefits (C. Thiemermann; 2001, Nature Medicine 7, 535-536). Nevertheless, it is conceivable, that gaseous CO could be useful for a number of clinical applications, such as organ transplantation or ischemic lung injury (see above).

The present invention represents a novel strategy, namely, the use of compounds, which exhibit therapeutic effects fully or in part by the generation of free carbon monoxide (CO). Carbon monoxide is generated from precursor compounds either by spontaneous release or by a metabolic process (i.e. with the involvement of one or more enzymes).

As used herein, the term "spontaneous release" means thermally, chemically, oxydatively induced release and also in some cases, such as in photodynamic therapy conditions, release by reactions induced by light. The release of CO from the compound is immediately assisted by donor molecules which are ubiquitous and unavoidable in the organism, from water to proteins or nucleotides.

As used herein, the term "release by metabolic process" means release with the involvement of one or more enzymes such as, for example, cytochrome P450 and glutathione S-transferase. The preferred embodiments of this invention are compounds comprising two components, a CO releasing moiety, and a second pharmaceutically important molecule e.g., a known drug carrier, and/or a known anti-inflammatory agent. A preferred class of conjugation partners for the CO-donors are nonsteroidal anti-inflammatory drugs (NSAIDs), including but not limited to aspirin. These drugs are known to accumulate in inflammatory lesions. CO-donors can also be attached to other anti-inflammatory agents, including but not limited to steroids and inhibitors of phosphodiesterases (PDE), in particular inhibitors of PDE4.

Delivery of CO in vivo to target tissues such as injured blood vessels or inflammatory lesions, is safe and beneficial in a large variety of diseases. Diseases that can be treated by CO donors are chronic inflammatory diseases, including, but not limited to, rheumatoid arthritis, multiple sclerosis, and other diseases with a strong inflammatory component, including but not limited to stroke, Alzheimers disease, atherosclerosis, coronary atherosclerosis, transplantation associated atherosclerosis, or restenosis after coronary stent implantation. In many indications, in particular those related to atherosclerosis and Alzheimer's disease, the compounds are useful for prevention.

Although the present invention comprises a number of different classes of compounds, the active principle in each case is carbon monoxide (CO), which acts alone or in conjunction with those moieties of the herein disclosed compounds that remain after the release of CO. Thus, according to the terminology used herein, a herein disclosed compound is modified, after administration to a mammal, into CO (product 1) and at least one other compound (product 2) which may or may not have pharmacological effects. In a preferred embodiment of the herein disclosed compounds, the herein disclosed compounds give rise, after administration to a mammal, to CO and product 2 which is identical with or closely related to known drugs or compounds with known pharmacological effects. Product 2 may be identical with or closely related to a known drug which has anti-inflammatory effects by interacting with a nuclear receptor, or a G protein coupled receptor, or a cyclooxygenase, or a phosphodiesterase. Examples of product 2 are aspirin, indomethacin, nimesulide, piroxicam, flurbiprofen, meloxicam, naproxen, vioxx, celecoxib and other cyclooxygenase inhibitors. Further examples of product 2 are compounds that are identical or closely related to cortisol, prednisolon, dexamethason, betamethasone, dehydroepiandrosterone (DHEA) or estradiol, diethylstilbestrol (DES), tamoxifen or other selective estrogen receptor modulators (SERMs), 1,25 dihroxyvitamin D, troglitazone or other thiazolidinediones (TZDs), or cyclopentenones. Further examples of product 2 are compounds identical with or closely related to pentoxifylline, rolipram or other phosphodiesterase inhibitors. Still other examples of product 2 are alendrolate or other biphosphonates. CO (product 1) may complement, or augment, or inhibit pharmacological effects of product 2. In some cases, CO can decrease adverse effects of product 2, which limit their therapeutic applicability when used alone, without the CO-releasing moiety. CO is generated either by spontaneous release or by metabolic process.

It is well known that CO is toxic when it reaches high levels in the environment and in the blood. The toxicity of CO is due to its ability to bind to the heme group of hemoglobin, the oxygen-carrying molecule in human blood. Hemoglobin that is associated with CO is referred to as carboxyhemoglobin or COHb. Because CO's affinity to bind with hemoglobin is 250 times greater than that of oxygen, relatively low airborne concentrations and long exposure times can result in substantial COHb concentrations in the blood. As COHb levels increase, less hemoglobin is available for the transport of oxygen. The acute health effects of CO exposure are headache, dizziness, decreased vigilance, decreased hand-eye coordination, weakness, confusion, disorientation, lethargy, chest pain (incardica patients), nausea, and visual disturbances. The severity of the symptoms depends mainly on the concentration of CO and the length of exposure time. COHb saturations of 0.5% to 3% can be found in nonsmoking adults and levels of 5 to 6% have been reported in smokers and in patients with hemolytic anemias. The symptoms of CO poisoning are usually only seen at COHb levels above 10%. Common sources of toxic CO levels in the environment are exhausts of internal combustion engines, gas water heaters and gas fires that are improperly vented.

Another source of CO intoxication is dichloromethane (DCM) also referred to as methylene chloride. DCM is a dense, colorless organic solvent. It has a mild, sweet odor, and evaporates very quickly. It is widely used as a paint stripper and is also a component of certain aerosols and pesticide products and is used in the manufacture of photographic films. DCM may enter the body when it is inhaled or ingested. It is readily absorbed through body membranes (e.g. stomach, intestine and lungs) and quickly enters the blood stream. Cytochrome P-450 and gluthatione S-transferase enzymes can both metabolize DCM to carbon monoxide or carbon dioxide. If DCM is breathed at levels above 500 ppm (500 parts per million parts air), it may cause effects much like those produced by CO poisoning. Extensive studies have been conducted on the toxicity, carcinogeneicity, and teratogenicity of DCM. Studies with rodents suggest that frequent exposure to DCM can cause changes in liver and kidney. However, studies of DCM exposed workers indicate that it is unlikely that DCM will cause serious liver or kidney damage in humans unless exposure is very high (Agency for Toxic Substances and Disease registry, Division of Toxicology, Atlanta, Ga., USA). Some rats and mice exposed to high concentrations of DCM throughout their lifetime developed cancer. However, DCM has not been shown to cause cancer in humans exposed at occupational levels. Teratology studies in mice and rats examined the effect of exposure to 1250 ppm DCM in the atmosphere, 7 hours per day on 6 to 15 days of gestation. No material or fetal toxicity attributable to the DCM exposure was reported (Schwetz et al 1975; Toxicol Appl. Pharmacol. 32, 84). The occupational Health and Safety Administration (OSHA 1991) has established exposure limits for persons who work with DCM. These include an 8-hr time-weighted average (TWA) of 25 ppm and an acceptable maximum peak above the ceiling of 125 ppm (5 minutes in any 2 hours) in the workplace air. In 1976, The National Institute of Occupational Safety and Health (NIOH 1976) recommended a 10-hour TWA exposure limit of 261 milligrams per cubic meter (75 ppm) and a 1,737 milligrams per cubic meter (500 ppm) peak (15-minute sampling) in the presence of CO concentrations less than or equal to 9.9 ppm.

One active principle of all compounds described in this invention is CO, and some are related to DCM. However, the above described toxicity of CO and DCM occurs at levels that are far above the levels required to achieve therapeutic and prophylactic effects. Moreover, the CO-releasing moieties described here are designed to release CO at specific sites in the body, such as inflamed tissues or pre-atherosclerotic lesions of arteries. Some of the CO-releasing moieties herein described accumulate in inflammatory lesions much like aspirin and many of the known NSAIDs. Others are targeted to specific tissues, e.g. bones in the case of biphosphonate derivates. Again others preferentially release CO in the presence of reactive oxygen species that are known to be generated at inflammatory sites and in atherosclerotic lesions. Development of the compounds described in the present invention for clinical applications will greatly benefit from the extensive work that has previously been done on CO and DCM toxicology.

Based on the above considerations, this invention provides compounds that can deliver CO in vivo to living tissues, undergoing inflammatory processes for instance. The present invention provides a number of different chemical systems that enable this purpose to be achieved. Preferred chemical systems are for example:

Class 1—CO containing organometallic complex. Such a compound can be dissolved in physiologically compatible support.

Class 2—CO containing organometallic complex linked to at least another pharmacologically important molecule. For example, said pharmacologically important molecule is a carrier, a drug (e.g., an anti-inflammatory agent). Furthermore, the CO containing organometallic complex and the at least other pharmacologically important molecule are optionally linked by means of an appropriate spacer.

Class 3—Supramolecule aggregates made of CO containing organometallic complexes optionally encapsulated in a cyclodextrin host and/or another appropriate inorganic or organic support.

Class 4—CO containing inorganic complexes bearing several categories of polidentate ligands containing N and/or S donors that function as reversible CO carriers.

Class 5—CO containing inorganic complex bearing ligands, e.g. polidentate ligands, containing N and/or S donors that function as reversible CO carriers, linked to at least another pharmacologically important molecule. For example, the pharmacologically important molecule is a carrier, a drug, (e.g. an anti-inflammatory agent). Furthermore, the CO containing organometallic complex and the at least other pharmacologically important molecule are optionally linked by means of an appropriate spacer.

Class 6—Organic substances that release CO either by an enzymatic process or by decarbonylation, dissolved in physiologically compatible supports.

Class 7—Organic substances that release CO either by an enzymatic process or by decarbonylation, e.g., dichloromethane, encapsulated either in cyclodextrin hosts and/or other appropriate inorganic or organic supports.

The following sections describe the guidelines for selecting these classes of compounds and provide specific examples.

Use of Organometallic Complexes for the Delivery of CO to Inflammated Tissues.

The role of transition metal complexes in medicine has been well recognized by many investigators and is presently undergoing a steady expansion. [C. Orvig, M. J. Abrams, Chem. Rev. 1999, 99, 2201 and following articles] Anti-carcinogenic, metal-based drugs are among the best known, in particularly the platinum derivatives, such as cis-platin and carboplatin. [E. Wong, C. M. Giandomenico, Chem. Rev. 1999, 99, 2451; E. R. Jamieson, S. J. Lippard, Chem. Rev. 1999, 99, 2467; J. Reedijk , Chem Rev. 1999, 99, 2499]. The development of medical applications for organometallic complexes has been slower, but important advances have been made using the two best and longer established families of organometallic complexes known: the metallocenes and the carbonyls. Anti-carcinogenic properties have been found for several metallocenes, the best example being that of titanocene dichloride [M. J. Clarke, F. Zhu, D. R. Frasca, Chem. Rev. 1999, 99, 2511]. With respect to the transition metal carbonyls that concern the present invention research has progressed more slowly. Carbonyl complexes of transition metals have been known for a long time and their derivatives have been widely studied both in fundamental organometallic chemistry and in a multitude of catalytic applications. The discovery of the first of such carbonyls, $Ni(CO)_4$ by C. Langer and L. Mond in 1888 led to the industrial process of Ni purification (the Mond process) which, requires very careful operation and safety procedures in order to deal with the very noxious and toxic nature of $Ni(CO)_4$. [W. E. Trout, Jr. J. Chem. Ed. 1938, 77]. The toxicity of these compounds well surpasses that of CO alone. Of course, CO is a well recognized toxic molecule, which is able to block the metal centers of hemeproteins, like hemoglobin and others. [E. Di Cera, M. L. Doyle, P. R. Connelly, S. J. Jill, Biochemistry, 1987, 26, 6494] Toxicity of a series of Cr, Mn, Fe and Ni organometallic carbonyls has been studied in mice and rats. The effects observed included selective necrosis of the non-conciliated bronchiolar epithelial (Clara) cells and other deleterious effects within 24 h of administration.[W. M. Haschek, P. J. Hakkinen, H. P. Witschi, R. P. Hanzlik, G. J. Traiger, Toxicol. Lett. 1982, 14, 85]. However, iron carbonyls can be used in human diets as iron supplements. These compounds have been shown to have a high bioavailability as measured by hemoglobin repletion in iron-deficient rats. [P. V. Sacks, D. N. Houchin, Am. J. Clin. Nutr. 1978, 31, 566]. Later studies emphasize the low toxicity of iron carbonyl powder and its absorption by the intestinal mucosa in rats, [H. A. Hubers, G. M. Brittenham, E. Csiba, C. A. Finch, J. Lab. Clin. Med. 1986, 108, 473] and reveal its usefulness and advantage over inorganic iron salts in the treatment of anemias in humans, which are caused by iron deficiency. [V. R. Gordeuk, G. M. Brittenham, C. E. McLaren, M. A. Hughes, J L. J. Keating, Blood, 1986, 67, 745].

U.S. Pat. No. 5,086,060 claims the use of iron carbonyl derivatives of several polyene molecules for the treatment of acne and psoriasis. However, more extensive investigations of the biological applications of organometallic carbonyls only started in the late 1980's with the work of Jaouen, Vessieres and their co-workers, on the development of organometallic reagents for immunoassay procedures, the so-called carbonylmetalloimmunoassay (CMIA). [G. Jaouen, A. Veesieres , I. S. Butler, Ace. Chem. Res., 1993, 26, 361] These studies led to several successive discoveries that are related to the applications of organometallic compounds to biological systems, leading to a new area of Bio-organometallic Chemistry. Recent applications include the development of new molecules not only for immunoassays but also for radiopharmaceutical, radiotherapeutic, imaging and other purposes, including bioactive molecules and markers. [K. Severin, R. Bergs, W. Beck, Angew. Chgem. Int. Ed. 1998, 37,1634; N. Metzler. Nolte, Angew. Chem. Int. Ed. 2001, 40,1040; G. Jaouen, S. Top, A. Vessieres, R. Alberto, J. Organomet. Chem. 2000, 600,23]. Carbonyl containing derivatives have proven very valuable and flexible in their uses. Their stability and compatibility with physiological media has been shown to be adequate for both in vitro and in vivo applications. These observations are of great interest for medicinal chemists, who generally regarded metal carbonyls to be too toxic for biological, and in particular clinical applications.

Indeed, very recent research on metal containing enzymes revealed the unexpected role of carbonyl complexes in nature, and some enzymes have been found to contain M-CO bonds in their active sites. Examples of such enzymes are the iron-nickel hydrogenase and the iron only hydrogenase [M. Frey, J. C. Fontecilla-Camps, A. Volbeda, in Handbook of Metalloproteins, A. Messerschmidt, R. Huber, T. Poulos, K. Wieghardt Eds. J. Wiley and Sons Ltd., 2001, 880; B. J. Lemon, J. W. Peters, ibidem p. 738].

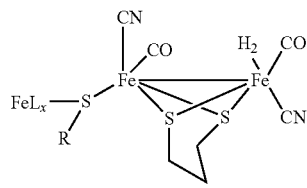

Desulfovibrio desulfuricans

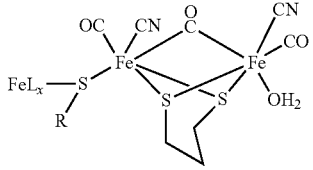

Clostridium pasteurianum

CO dehydrogenases carry out the oxidation of CO to $CO_2$ plus 2 electrons and 2 $H^+$. Two of these enzymes have also been structurally characterized. They contain Cu and Ni in their active centers and involve intermediate M-CO species [H. Dobbek, L. Gremer, O. Meyer, R. Huber, in Handbook of Metalloproteins, A. Messerschmidt, R. Huber, T. Poulos, K. Wieghardt Eds. J. Wiley and Sons Ltd., 2001, p. 1136; H. Dobbek, V. Svetlitchnyi, L. Gremer, R. Huber, O. Meyer, Science, 2001, 293, 1281].

It is now clear that may 18 electron organometallic CO derivatives are stable under physiological conditions. On the other hand, a general property of these complexes is their decomposition and accelerated CO release under light irradiation and under oxidative conditions. It is well known that oxygen based radicals are generated in inflammatory processes and that they play a crucial role in the pathogenesis of atherosclerosis. Thus, organometallic carbonyl derivatives release CO in inflamed tissues and atheriosclerotic lesions. This line of thought led to the discovery of three different classes of organometallic drugs.

Class 1—CO Containing Organometallic Complexes Dissolved in Physiologically Compatible Supports This class of compounds comprises either simple 18 electron organometallic carbonyl complexes or modifications thereof designed to improve either their solubility in physiological media or their compatibility with membranes and biomolecules or tissues. The metals that may be used include first transition row biologically active metals (V, Cr, Mn, Fe, Co, Ni, Cu) as well as second (Mo, Ru, Rh, Pd) and third row elements (W, Re, Pt Au), that appropriately bind the CO ligand. A large number of these compounds bears the cyclopentadienyl ligand (Cp) or derivatives thereof (idenyl, CpR5, and the like) hereby abbreviated as CpR(X), which enable the above-mentioned modifications, and impart some steric protection to the metal center with the corresponding higher reactivity control. The oxidation state of the metal in most of the complexes resembles the one usually found under biological conditions thereby facilitating later metabolization, after CO release.

In the examples listed immediately below, the term "pseudo-halide" is general name given to mono-anionic ligands isoelectronic with the halides, e.g., thiocyanates, cyanates, cyanides, azides, etc. The term "hydrocarbyl chain" is the general name of a hydrocarbon radical comprising aliphatic $CH_2$ and/or aromatic residues, e.g., $(CH_2)_n$, n=2, 3, etc. or $(CH_2)_n$, $(C_6H_4)_m$, $C_6H_5CH_2$, etc. Alkyl is the general name given to the radical of an aliphatic hydrocarbon chain, e.g. methyl, ethyl, etc. Aryl is the general name given to a radical of an aromatic ring, e.g., phenyl, tolyl, xylyl, etc.

Leading Examples

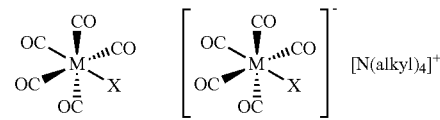

M = Mn, Re
X = Cl, Br, I, alkyl, aryl,
acyl, C-glycoside,
carboxylate, SR, OR
(R = alkyl, aryl)

M = Cr, Mo, W
X = Cl, Br, I, OR, SR,
(R = alkyl, aryl)
carboxylate, sugar

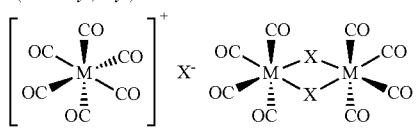

M = Mn, Re
X = halide or weakly
coordinating anion

M = Mn, Re
X = halide, SR, OR
R = alkyl, aryl

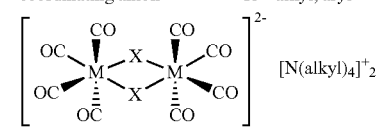

M = Mo, W
X = SR, OR
R = alkyl, aryl

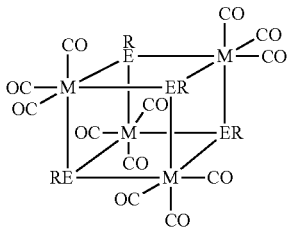

M = Mn, Re
E = S, O
R = H, alkyl, aryl

-continued

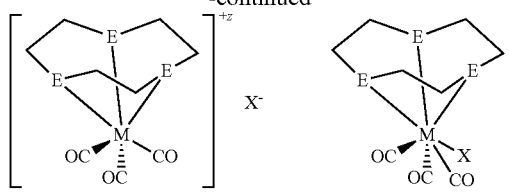

M = Mn, Re (Z = +1); Cr, Mo, W (Z = 0)
E = combinations of N, S and O between 1 to 3 each
X = halide or weakly coordinating anion (for Z = +1)

M = Cr, Mo, W
E = combinations of N, S and O between 1 to 3 each
X = halide, pseudohalide, OR, SR, carboxylate, R = alkyl, aryl

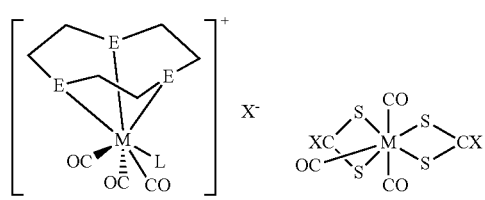

M = Cr, Mo, W
E = combinations of N, S and O between 1 to 3 each
L = CO, olefin, alkyne, or monodentate 2 electron donor of O, S, N or P
X = halide or weakly coordinating anion M = Mo, W
X = $NR_2$, OR
R = alkyl, aryl

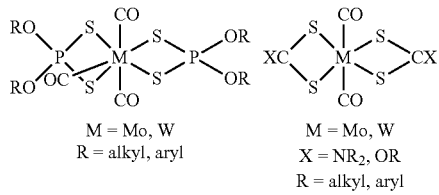

M = Mo, W
R = alkyl, aryl

M = Mo, W
X = $NR_2$, OR
R = alkyl, aryl

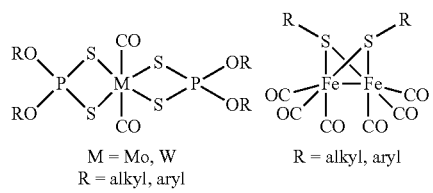

M = Mo, W
R = alkyl, aryl

R = alkyl, aryl

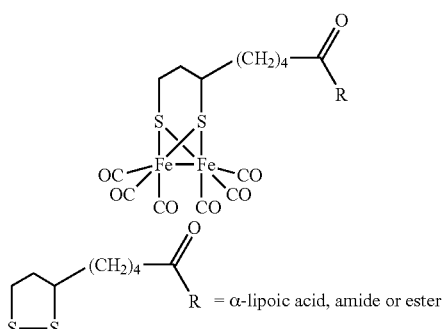

R = α-lipoic acid, amide or ester

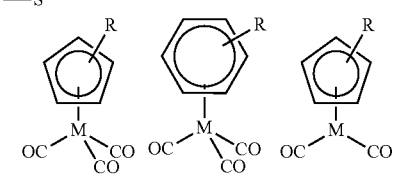

M = Mn, Re    M = Cr, Mo, W    M = Co, Rh

R = H, alkyl, acyl, formyl, carboxylate, sugar, peptide, halide

-continued

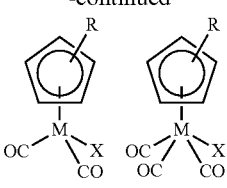

M = Fe, Ru    M = Cr, Mo, W

X = alkyl, aryl, halide, OR', SR', $O_2CR'$, $S_2CNR'_2$, $S_2P(OR')_2$
R' = alkyl, aryl
R = H, alkyl, acyl, formyl, carboxylate, sugar, peptide, halide

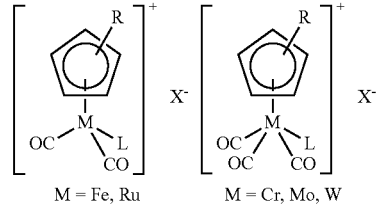

M = Fe, Ru    M = Cr, Mo, W

R = H, alkyl, acyl, formyl, carboxylate, sugar, peptide, halide
L = CO, olefin, alkyne, or monodentate 2 electron donor of O, S, N or P
X = halide or weakly coordinating anion

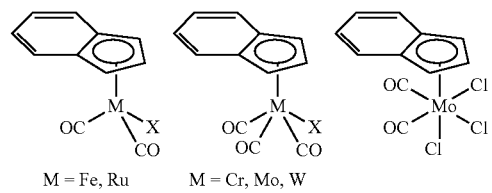

M = Fe, Ru    M = Cr, Mo, W

X = alkyl, aryl, halide, OR', SR', $O_2CR'$, $S_2CNR'_2$, $S_2P(OR')_2$
R' = alkyl, aryl

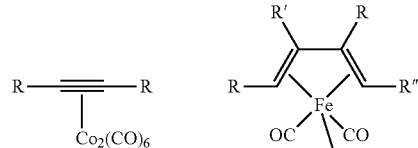

R = H, alkyl, aryl, OR, $CO_2R$    R or R' = H, hydrocarbyl chain
R'' = H, alkyl, aryl, OR, $CO_2R$

[$PtCl_2(CO)$]$_2$    $Au(OSO_2F)(CO)$    MCl(CO)

M = Cu, Au

Several modifications can be envisaged to improve higher biological compatibility and solubility. One preferred possibility is to attach carboxylic, peptide or sugar derivatives to the cyclopentadienyl moiety. Examples are depicted for one Mn complex; similar derivatives can be made with compounds containing other metals, as well as for indenyl and other CpR(X) derivatives.

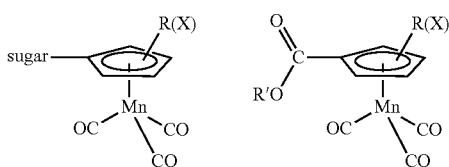

R(X) = H, alkyl, aryl, formyl, acyl, carboxylate or fused C6 aromatic ring (indenyl ligand)
R' = H, alkyl, peptide, sugar Class 2—CO Containing Organometallic Complexes Linked to other Pharmacologically Important Molecules.

This class of compounds takes advantage of the synergistic effects arising from the combination of two biologically active molecules, which both have beneficial effects. Examples for such drug-drug conjugates have been described in U.S. Pat. No. 6,051,576.

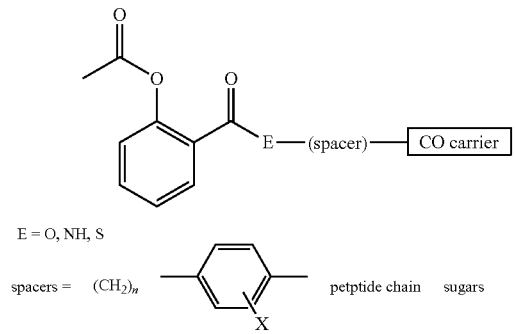

The above mentioned spacers comprise a variety of functions under the following specifications: the value of "n" in the linear hydrocarbon chain is an integer more specifically 1, 2, 3, 4: X is a general symbol for a substituent at the aromatic ring, namely, alkyl, aryl, alkoxy, aryloxl, halogen atom, thiolate; "peptide chain" represents a short chain of natural amino acids ranging from 1 to 4; by "sugars" it is meant the use of a mono-; di- or polysaccharide either protected or modified with adequate protection to increase lipophilicity and/or assure chemical stability of the drug-drug conjugate molecule, for example, with protective groups, such as esters, acetals, and silyl derivatives.

The definition of X given immediately above can be extended to carboxylates and amino acids in the cases where X is directly bound to the metal as in some of the leading examples depicted in the next scheme.

Leading Examples

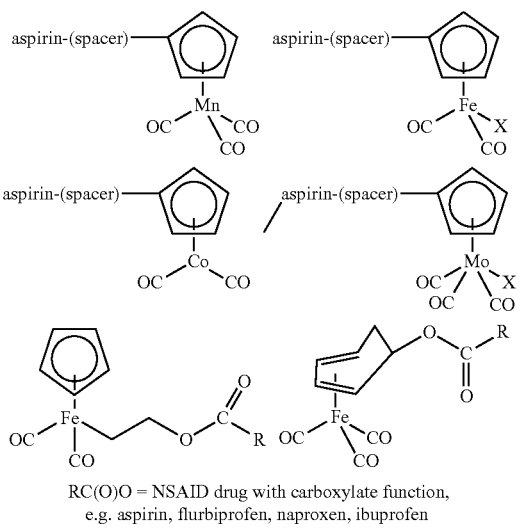

RC(O)O = NSAID drug with carboxylate function, e.g. aspirin, flurbiprofen, naproxen, ibuprofen

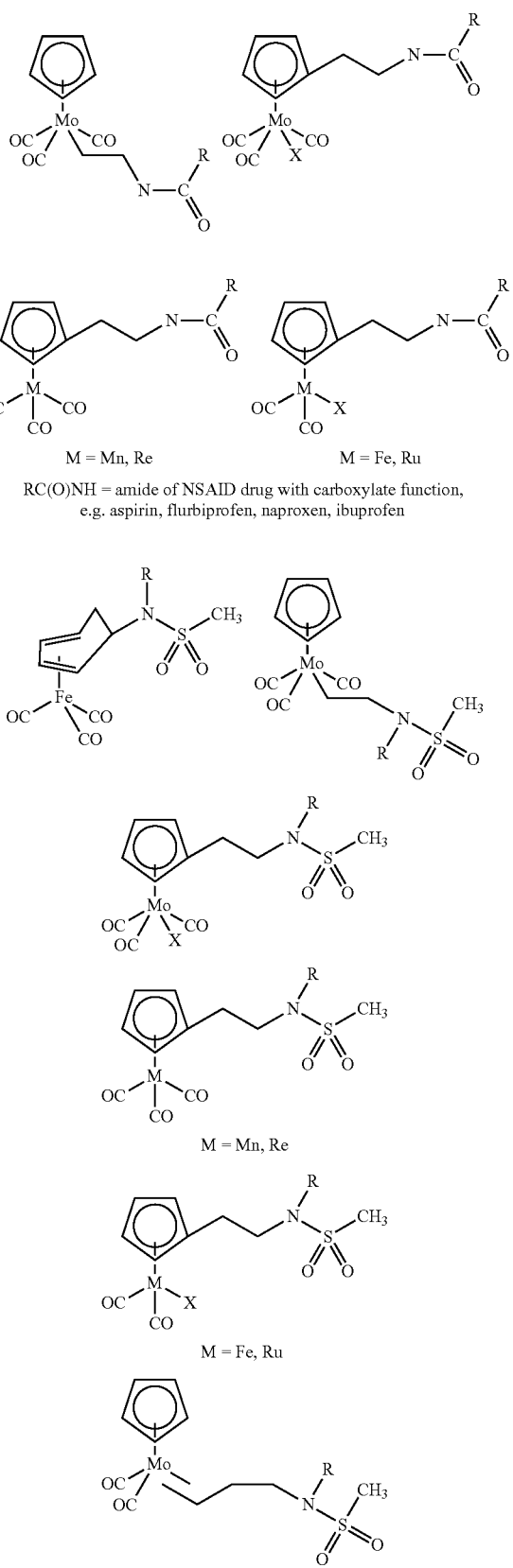

RC(O)NH = amide of NSAID drug with carboxylate function, e.g. aspirin, flurbiprofen, naproxen, ibuprofen $CH_3SO_2NR$ = anion of nimesulide, or Cox-2 inhibitors, e.g. NS398, L-745,337

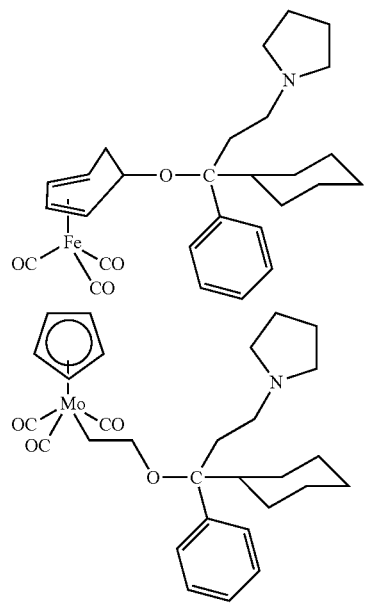

Anticholinergic drugs inter alia Procyclidine derivatives

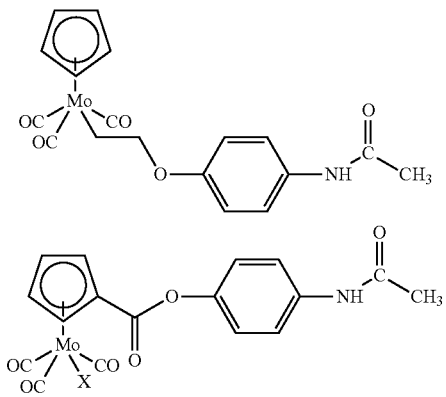

Paracetamol derivatives; X = halide, OR, SR (R = alkyl, aryl)

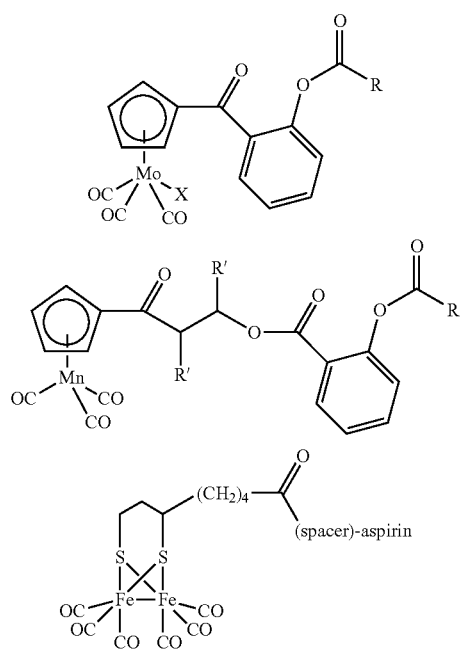

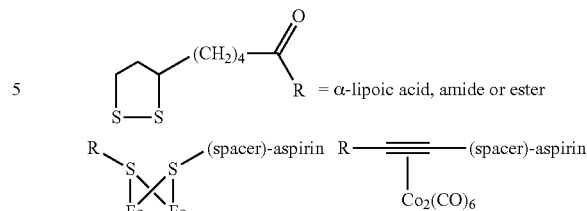

R = α-lipoic acid, amide or ester

Aspirin derived conjugates. R, R' = alkyl; X = halide, OR, SR

A second group of compounds bears the bioactive molecule, e.g. aspirin, diphosphonate, bound directly to the metal, which can be achieved in several different manners as schematized below for the case of some iron and molybdenum cyclopentadienyl carbonyls, among others. The term "hydrocarbyl chain" is the general name of a hydrocarbon radical comprising aliphatic $CH_2$ and/or aromatic residues, e.g., $(CH_2)_n$, n=2, 3, etc. or $(CH_2)_n$, $(C_6H_4)_m$, $C_6H_5CH_2$, etc.

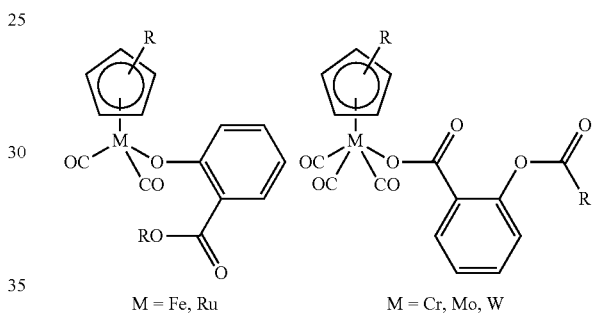

M = Fe, Ru         M = Cr, Mo, W

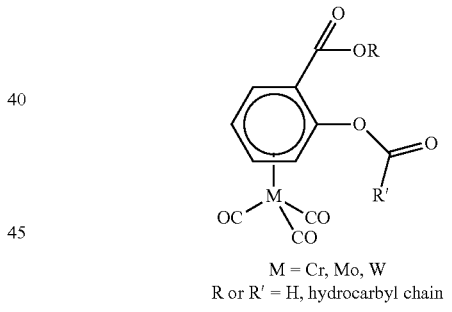

M = Cr, Mo, W
R or R' = H, hydrocarbyl chain

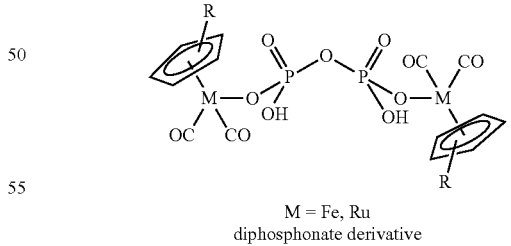

M = Fe, Ru
diphosphonate derivative

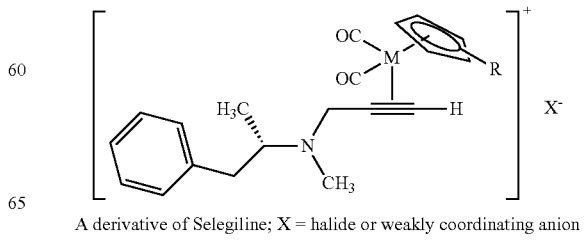

A derivative of Selegiline; X = halide or weakly coordinating anion

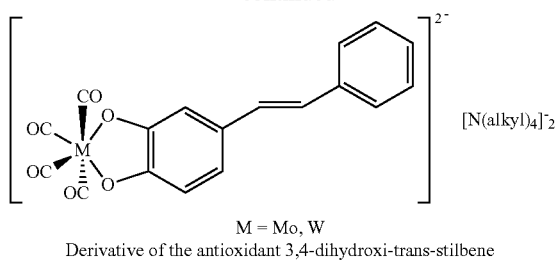

M = Mo, W
Derivative of the antioxidant 3,4-dihydroxi-trans-stilbene

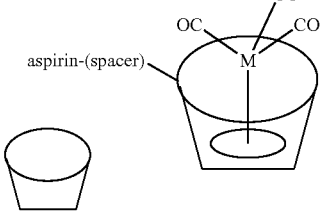

β-cyclodextrin

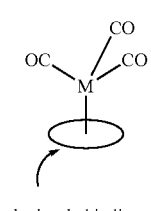

hydrophobic ligand

Class 3: Encapsulated Supramolecular Aggregates made of CO Containing Organometallic Complexes.

Controlled delivery of drugs into the organism in an important issue, especially in the case of drugs, which have undesired toxic effects if present systemically or at high local concentrations. CO release is a potential problem inasmuch as it can be toxic at high concentrations (see above). For certain applications, a slow release of CO in the blood or in specific target tissues is desirable. Encapsulation within host molecules that are non-toxic is one way to achieve a sustained release of active drugs in the organism. This strategy minimizes the undesired effects that my result from abrupt increases in the concentration and/or availability of a potentially toxic drug.

Cyclodextrins are well known hosts for many drugs and organic molecules and, recently have been applied to host organometallic molecules and enhance their delivery through physiological barriers or membranes. In this respect cyclodextrin has been found to be beneficial for increasing delivery of lipophilic drugs at the skin barriers. [T. Loftsson, M. Masson, Int. J. Pharm. 2001, 225, 15]. Cyclodextrin mediated supramolecular arrangements protect organometallic molecules for prolonged time periods and mask their reactivity, thereby increasing their selectivity towards specific reagents. The hydrophobic part of carbonyl complexes as those exemplified under Class 1 above, fit inside (3- or γ-cyclodextrin, or similar structures, with the CO groups facing the reaction medium and the organic ligands buried in the cavity. The resulting reduction in reactivity allows for the extension of the range of therapeutic CO-release complexes to cationic and anionic ones. Such charged complexes are more reactive and lose CO faster that the neutral ones when unprotected.

Liposomes and other polymeric nanoparticle aggregates are also useful carriers to target the delivery of CO-releasing organometallic complexes and the combined use of cyclodextrins with such aggregates has been considered as a very promising possibility for drug release. [D. Duchene, G. Ponchel, D. Wouessidjewe, Adv. Drug Delivery Rev. 1999, 36, 29.]

Conceptual Examples

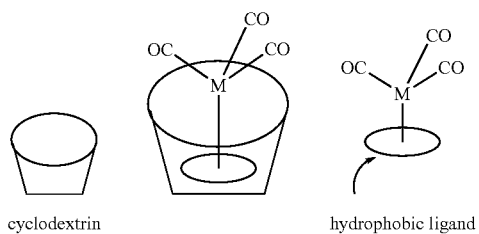

cyclodextrin     hydrophobic ligand

The actual examples cover organometallic molecules as $(C_6H_{6-x}R_x)M(CO)_3$ (M=Cr, Mo, W); $(CpR_5)M(CO)_3X$ (M=Cr, Mo, W); $(CpR_5)M(CO)_2X$ (M=Fe, Ru); $(CpR_5)M(CO)_2$ (M=Co, Rh) where R represents H, alkyl or other small functional group like methoxide, halide, carboxylic esters.

Mesoporous materials are chemically inert three dimensional molecules with infinite arrays of atoms creating channels and cavities of well defined pore size. These molecules are well suited to host organic and organometallic molecules in their pores. In the presence of biological fluids, smaller molecules undergoing acid-base and/or polar interactions with the inner walls of the pores slowly displace the included drugs, resulting in a controlled delivery of the active principle. Such aggregates have been prepared from M41S materials using organometallic molecules like those depicted under system 1 above. Examples include MCM-41 (linear tubes) and MCM-48 (cavities and pores)

Class 4—CO Containing Inorganic Complexes Bearing Ligands Containing N and/or S Donors that Function as Reversible CO Carriers.

Classical inorganic complexes bearing macrocyclic ligands on an equatorial plane of an octahedral coordination sphere are known to reversibly bind CO much in the same way as hemoglobin. The capacity to bind CO can be "tuned" by the nature of both the macrocycle and the ancillary ligand trans to CO. A similar behavior has also been reported for other Fe(II) complexes bearing ligands that are much simpler than the porphyrin macrocycles that are the CO acceptor sites in hemoglobin and other heme containing proteins. In order to develop suitable CO delivering drugs, the later type of non-hemic complexes was chosen to avoid interference with the biological heme carriers, heme metabolism, and potential toxicity of heme or heme-like molecule. The complexes selected bear bidentate N donors (diamines, diglyoximes) or bidentate N,S donors of biological significance, like aminothiols or cysteine. Ancillary ligands are N donors also of biological significance like imidazole, hystidine, and others. The complexes are soluble in aqueous media.

In the examples immediately below, the term pyridines refers to derivatives of the $C_5H_5N$ ring (pyridine) bearing alkyl (R), alkoxy (OR), carboxy (C(O)OR), nitro ($NO_2$), halogen (X), substituents directly bound to the one or more positions of the C5 carbon ring, e.g. $CH_3C_5H_4N$, $O_2NC_5H_4N$. Amino-thiols refers to compounds bearing both the $NH_2$ (amino) and SH (thiol) functions bound to a hydrocarbon skeleton, e.g. $H_2NCH_2CH_2SH$, $1,2-C_6H_4(NH_2)(OH)$. A similar definition applies to amino alcohols, whereby the SH function is replaced by the OH (alcohol) function. The term amino acids refers to naturally occurring single amino acids coordinated in a bidentate fashion by the $NH_2$ and the COO functions as schematically depicted. Glyoximes are bidentate N donors, bearing either alkyl or aryl substituents on the hydrocarbon chain binding the two N atoms, as depicted in the first example below for a diaryl glyoxime. Diimines present a similar structure whereby the OH groups in the diglyoximes are replaced by alkyl or aryl groups. An extension of this family of ligands includes also 2,2'-bypiridines, e.g., 2,2'-dipyridyl, and phenanthrolines.

Leading Examples

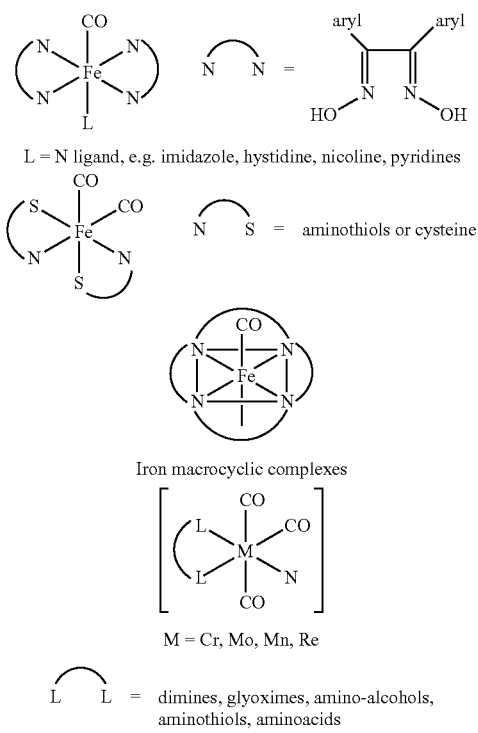

Class 5—CO Containing Inorganic Complexes Bearing Ligands Containing N and/or S Donors that Function as Reversible CO Carriers, Modified by Linkage to other Pharmacologically Important Molecules.

Following the lines of thought outlined above for Class 2 compounds, new CO carries of the type described as Class 4, but modified by linking the ligands to other biologically active molecules via an appropriate spacer, were prepared.

Leading Examples

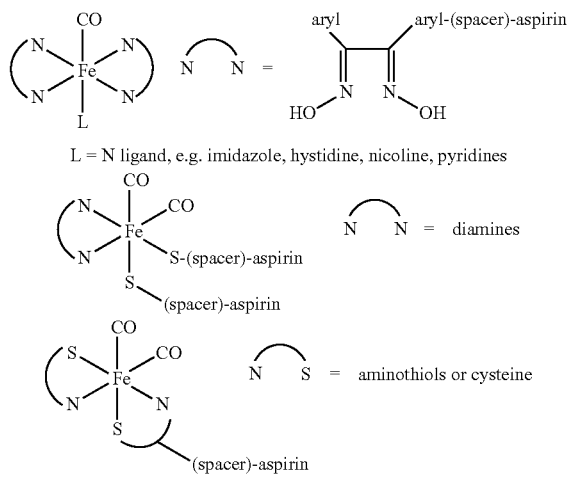

Class 6—Organic Substances that Release CO Either by an Enzymatic Process or by Decarbonylation.

In spite of the fact that decarbonylation is not a very common type of reaction in organic chemistry, some organic substances are known to liberate CO upon treatment with either bases, acids, or radical initiators depending on their nature. These substances fall into the flowing groups: polyhalomethanes of the general form $CH_nX_yX^1_{4-(n+y)}$ (X and or $X^1$=F, Cl, Br, I) trichloroacetic acid, and its salts, organic and inorganic esters and sulfinates thereof, triaryl carboxylic acid, formic acid, oxalic acid, α-hydroxyacids and oc-ketoacids, esters and salts thereof, under acid conditions; trialkyl and trialkoxybenzaldehydes under acid catalysis; aliphatic aldehydes with radical initiators, e.g., peroxides or light. For the polyhalomethanes, the values of n and y vary in the following way: for n=0, y=1, 2, 3, 4; for n=1, y=1, 2, 3; for n=2, y=1, 2; for n=3, y=1. In the above examples, the term "salt" applies to the ionic derivative of the conjugate base of a given protonic acid, namely a carboxylate, with a main group element ion, namely $Na^+$, $K^+$. Alkyl is the general name given to the radical of an aliphatic hydrocarbon chain, e.g. methyl, ethyl, propyl, butyl, etc. The alkyl group can be branched or straight chain. Aryl is the general name given to a radical of an aromatic ring, e.g., phenyl, tolyl, xylyl, etc. The aryl group will typically have about 6 to about 10 carbon atoms. Ester is the general name given to the functional group —C(O)OR (where R=alkyl, aryl).

The first two categories produce dichlorocarbene, which, under physiological conditions, will be metabolized to CO. In the case of dichloromethane, cytochrome P-450 has been shown to be responsible for the liberation of CO in vivo.

The third group of compounds releases CO under acid catalysis and is sensitive to the aryl substitution pattern. Most likely this is also true for the fourth group which includes trialkyl and triaryl substituted aldehydes. Strong activating groups on the aryl ring favor CO liberation under acid conditions. More importantly, the radical initiated decomposition of aliphatic aldehydes, induced by peroxides or light, produces CO under very mild conditions. The value of "n", the number of substituents (alkyl, aryl, alkoxy, aryloxy) on the aromatic ring, can vary from 0 to 5, preferably 1, 2, or 3.

Leading Examples

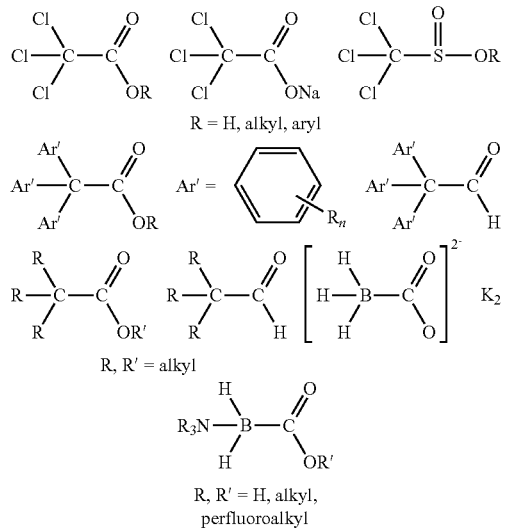

Class 7—Encapsulated Organic Substances that Release CO either by an Enzymatic Process or by Decarbonylation This system comprises the same molecules described under Class 6, but includes their encapsulation in host-guest supermolecules, liposomes, cyclodextrins, and other polymeric material that are able to produce nanoencapulated drug delivery vectors.

Properties of the compounds of the inventions are evaluated by methods known by the one skilled in the art. For example, anti-inflammatory activity can be determined by the method described by Winter et al. (*Proc. Soc. Exp. Biol. Med.* 111, 544, 1962) or by Patrono et al. ∴ *Thrombosis Res.* 17, 317, 1980).

Drug Formulations

Compounds useful in the practice of this invention can be formulated into pharmaceutical compositions together with pharmaceutically acceptable carriers for oral administration in solid or liquid form, or for intravenous, intramuscular, subcutaneous, transdermal, or topical administration. Carriers for oral application are preferred.

Pharmaceutically acceptable carriers for oral administration include capsules, tablets, pills, powders, troches, and granules. In the case of solid dosage forms, the carrier can comprise at least one inert diluent such as sucrose, lactose or starch. Such carriers can also comprise, as is normal practice, additional substances other than diluents, e.g. lubricating agents such as magnesium stearate. In the case of capsules, tablets, troches and pills, the carrier can also comprise buffering agents. Carriers, such as tablets, pills and granules, can be prepared with enteric coatings on the surfaces of the tablets, pills or granules. Alternatively, the enteric coated compounds can be pressed into tablets, pills, or granules. Pharmaceutically acceptable carriers include liquid dosage forms for oral administration, e.g. emulsions, solutions, suspensions, syrups and elixirs containing inert diluents commonly used in the art, such as water. Besides such inert diluents, compositions can also include adjuvants, such as wetting agents, emulsifying and suspending agents, and sweetening, flavoring agents.

Pharmaceutically acceptable carriers for topical administration include DMSO, alcohol or propylene glycol and the like that can be employed with patches or other liquid retaining material to hold the medicament in place on the skin. New approaches based on nanoparticles, nanoencapsulates and the like are also considered convenient for the protection of the active principle and its slow release in the organism or specific tissues.

Pharmaceutically acceptable carriers for intravenous administration include solutions containing pharmaceutically acceptable salts or sugars.

Pharmaceutically acceptable carriers for intramuscular or subcutaneous injection include salts, oils, or sugars.

When used in its acid form, a compound of the present invention can be employed in the form of a pharmaceutically acceptable salt of the acid. Carriers such as solvents, water, buffers, alkanols, cyclodextrins and aralkanols can be used. Other auxiliary, non-toxic agents may be included, for example, polyethylene glycols or wetting agents.

The pharmaceutically acceptable carriers and compounds described in the present invention are formulated into unit dosage forms for administration to the patients. The dosage levels of active ingredients (i.e. compounds of the present invention) in the unit dosage may be varied so as to obtain an amount of active ingredient that is effective to achieve a therapeutic effect in accordance with the desired method of administration. The selected dosage level therefore mainly depends upon the nature of the active ingredient, the route of administration, and the desired duration of treatment. If desired, the unit dosage can be such that the daily requirement for an active compound is in one dose, or divided among multiple doses for administration, e.g. two to four times per day.

Preferably, the compounds are administered orally once a day. The preferred dose levels will be determined in animals for representative compounds from each class. All compounds described in the present invention generate CO after administration to the body. Although CO is generated preferentially at the sites of inflammation, some of the CO generated will bind to hemoglobin in red blood cells. Thus, dose finding studies will initially be guided by measurement of carboxyhemoglobin (COHb) levels in the blood. Methods for the measurement of COHb levels in the blood are well known and are being used on a regular basis in diagnostic laboratories. In normal healthy humans COHb levels are about 0.5% in healthy nonsmokers and up to 9% in smokers. Preferred dose levels of the compounds described in the present invention are such that no significant rise in COHb levels is observed. However, in some applications a transient rise in COHb levels up to 10% may be tolerated. This level of COHb is not associated with any symptoms.

Compounds in Classes 1 and 4 are administered in a dosage ranging between 5 and 25 mmol/day depending on the nature of the CO containing compound and its molar CO content. The same range of dosage of the CO containing molecule is applied for Class 3 compounds. For aspirin conjugates in classes 2 and 5, the dose can vary from a lower 120 mg/day up to 10 g/day with preferred values in the range of 1 g/day for adults. These are indicative values dependent on the nature of the CO carrier molecular fragment and comply with the usual ranges for aspirin dosage. For the polyhalomethane and similar compounds in Class 6, e.g., dichloromethane, the dose range varies between 0.01 to 10 mmol/kg per os, with a preferred dose level of 0.1 mmol/kg. The same range of dosage of active principle is applied in the Class 7 compounds.

The present invention is further illustrated by the examples depicted in the following scheme, which are illustrative only.

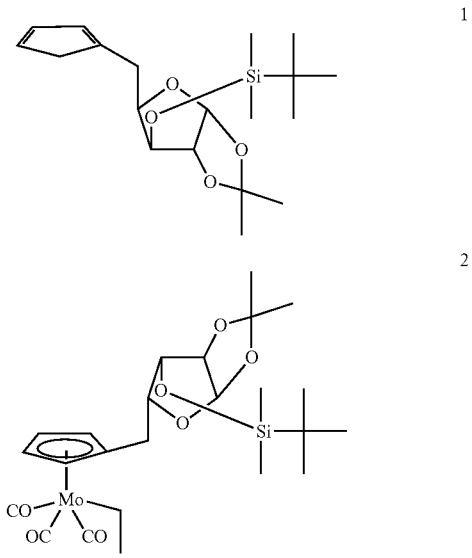

-continued

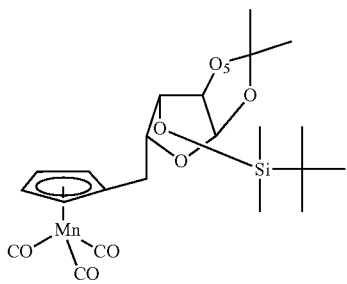

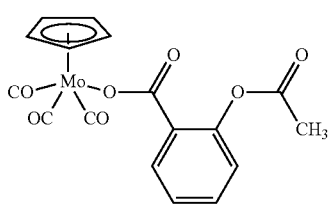

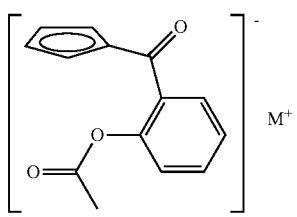

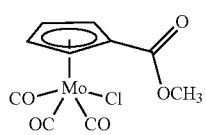

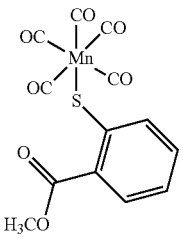

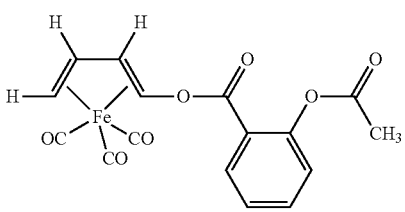

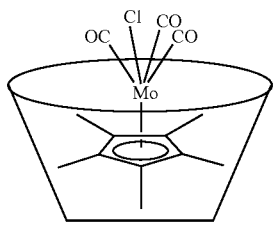

EXAMPLE 1

Preparation of the Sugar Derivatized Cyclopentadiene Ligand 1

To a solution of CpNa (2.2 g, 24.3 mmol) in DMF (8 ml) was added a solution of the protected sugar (3.7 g, 8.1 mmol) in DMF (20 ml) at −30° C. The reaction mixture was stirred at low temperature for 15 min and then was allowed to warm up to room temperature and stirred for a further 2 h. Destilled water (40 ml) was added to the mixture to destroy the excess of CpNa. The mixture was extracted with dichloromethane (2×100 ml) and the organic layer was dried with $Na_2SO_4$ and DMF was evaporated under vacuum. The residue was purified by column chromatography on silica (AcOEt/n-hexane 1:8) to give the title compound 1 as a yellow oil. Yield g (75%). Since several isomers are present, the compound was best characterized and stabilized by transformation into its $Tl^+$ salt by action of $TlOC_2H_5$ or the $Na^+$ salt by action of NaH. The ionic derivative of cyclopentadiene 1 as the $Tl^+$ salt, hereby abbreviated as $Cp^sTl$, was easily obtained in analyticaly pure form. Anal. Calc. For $C_{19}H_{31}SiO_4Tl$: C, 41.12; H, 5.41. Found: C, 40.71; H, 5.29

From the cyclopentadiene ligand 1, other Class 1 cyclopentadienyl complexes bearing sugar substituents on the ring are prepared by standard organometallic procedures as in Example 2 below for a xylose-protected derivative.

From the anion of the cyclopentadiene derivative 1, hereby abbreviated to CpS, prepared either as the $Tl^+$ salt by action of $TlOC_2H_5$ or as the $Na^+$ salt by action of NaH, a wide variety of Class 1 cyclopentadienyl complexes bearing sugar substituents on the ring are prepared by standard organometallic procedures as in Example 3 below.

EXAMPLE 2

Preparation of Compound 2

To a solution of $Mo(CO)_3(NCMe)_3$ (0.4 g, 1.14 mmol) in toluene (20 ml) was added a solution of $Cp^sH$ (0.4 g, 1.14 mmol) in toluene (20 ml) at room temperature. The reaction mixture was stirred for 2 h and the orange solution was filtered through Celite. The filtrate was concentrated to dryness and the residue was dissolved in dichloromethane (50 ml). Solid $CHI_3$ (0.37 g, mmol) was added to the dichloromethane solution and the colour immediately turned to a deep red. The reaction mixture was stirred for a further 30 min to ensure completion of the reaction and the solvent was removed under vacuum. The title compound 3 was isolated as a red solid. Yield (68%). Anal. Calc. for $C_{22}H_{31}MoO_7SiI$: C, 40.13; H, 4.75. Found: C, 39.84; H, 4.45. Selected IR (KBr, cm$^{-1}$): 2039, 1963, 1884, vs, v(CO);

EXAMPLE 3

Preparation of Compound 3

Solid $MnBr(CO)_5$ (0.14 g, 0.54 mmol) was added as a solid to a stirred solution of $Cp^sTl$ (0.3 g, 0.54 mmol) in THF (40 ml) at room temperature. The reaction mixture was stirred for 16 h and the solvent was removed under vacuum. The residue was extracted in dichloromethane to yield the title compound 2 as a waxy yellow solid. Yield g (73%). Anal. Calc. for $C_{22}H_{31}MnO_7Si$: C, 53.98; H, 6.32. Found: C, 53.51; H, 6.15. Selected IR (KBr, cm$^{-1}$): 2019, 1928, vs, v(CO).

EXAMPLE 4

Preparation of Compound 4

Dichloromethane (20 ml) was added to a mixture of $(C_5H_5)$ Mo(CO)$_3$Cl (0.40 g, 1.42 mmol) and silver salt of the o-acetylsalicylic acid (0.40 g, 1.42 mmol) and the reaction mixture was stirred for 2 h. at room temperature. The white precipitate of AgCi was separated by filtration and the filtrate was concentrated to dryness to yield compound 4 in 85% yield (0.51 g). Anal. Calc. for $C_{17}H_{12}O_7Mo$: C, 48.12; H, 2.83; Found: C, 47.90; H, 2.76.

EXAMPLE 5

Preparation of the Aspirin Derivatized Cyclopentadienyl Ligand 5

To a mixture of CpTl (1 g, 3.71 mmol) and acetylsalicyloyl chloride (0.73 g, 3.71 mmol) toluene was added (30 ml). The reaction mixture was stirred overnight at room temperature. The solution was filtered through celite and the filtrate was concentrated to dryness to yield the cyclopentadiene derivatized with aspirin as a white solid in 82% yield (0.69 g). Since several isomers are present the compound is best characterized as its Tl derivative. This is prepared by dissolving the compound in tetrahydrofuran (30 ml) treating it with TlOC$_2$H$_5$. A yellow precipitate of 5$^-$ as the Tl$^+$ salt was immediately formed in 77% yield.

From 5Tl or its Na analogs, prepared by replacement of TlOC$_2$H$_5$ with NaH, a variety of compounds can be made, using straightforward organometallic chemistry methods, that contain the aspirin bound to the cyclopentadienyl ring.

EXAMPLE 6

Preparation of Compound 6

[Bu$_4$N][Mo(CO)$_5$I] (0.96 g; 1.60 mmol) and [Cp(COOMe)]Na (0.28 g; 1.90 mmol) are dissolved in 20 mL THF each. The 2 solutions are mixed in a reaction flask and refluxed overnight (18 hours). The yellow brown solution is evaporated under vacuum and an oily residue is obtained. This is treated with 20 mL ether, 20 mL distilled water and 0.1 mL acetic acid. After 20 min of stirring, 5 mL of CCl$_4$ are added and the colour of the emulsion turns to red. The mixture is stirred for further 20 min and the ether phase is separated. The remaining aqueous phase is extracted with ether (5×20 mL). The ether extracts are combined and evaporated under vacuum. The red residue is redissolved in 20 mL of acetone, then some active charcoal and anhydrous Na$_2$SO$_4$ are added. The mixture is stirred for 30 min and then filtered with a canula. The red filtrate is evaporated to dryness and washed with cold hexane. Yield (based on [Me$_4$N][Mo(CO)$_5$I]): 41%. Anal. Calc. for $C_{10}H_7ClMoO_5$ (338.56): C 35.48; H 2.08. Found: C 35.83; H 2.50. Selected IR (KBr/cm$^{-1}$): ν=2058 (s), 1961 (s), 1974 (s), 1856 (w), 1725 (s), $^1$H NMR (CDCl$_3$, 300 MHz, r.t): δ=6.04-6.02 (m, 2H, Cp-H$_{3,4}$); 5.74-5.69 (m, 2H, Cp-H$_{1,5}$); 3.83 (s, 3H, H$_{COOCH3}$).

EXAMPLE 7

Preparation of Compound 7

The sodium salt NaSC$_6$H$_4$C(O)OMe was prepared in the following way: to 1.66 mL of HSC$_6$H$_4$C(O)OMe (2.035 g; 12.097 mmol) THF (100 mL) was added. The pale yellow solution was cooled to −10° C. and NaH (0.290 g; 95% pure, 1 equivalent) added slowly. The mixture turned into a bright yellow suspension from which a yellow solid precipitated within a few minutes. After 1 hr. the solvent was evaporated and the powder residue dried under vacuum (quantitative yield). NaSC$_6$H$_4$C(O)OMe (0.384 g; 2.017 mmol) was charged into a schlenk tube and THF (30 mL) added. The yellow suspension was cooled to 0° C., and Mn(CO)$_5$Br (0.554 g; 2.017 mmol) was added slowly in the solid state. The reaction mixture immediately turned green and progressively became yellow. Stirring was continued for 18 hours at r.t. after which time the orange suspension was filtered off. The orange solution was cooled at −30° C. and a small amount of an impurity precipitated. This was filtered off and the solution evaporated to dryness, yielding [Mn(CO)$_5$(SC$_6$H$_4$C(O)OMe] in 80% yield. Anal. Calc for C13H7MnO7S: C, 43.11; H, 1.95; S, 8.85. Found: C, 42.87; H, 1.84; S, 8.26. Selected IR (KBr, cm$^{-1}$): 2046 (m), 1994 (s), 1928 (s) 1904 (s); 1708 (m). 1H NMR (acetone d$^6$; 300 MHz): 8.53 (d,1H,3J=7.8 Hz, SCH); 7.40-7.31 (m,2H,C$_6$H$_4$); 7.21 (dd, 1H, C$_6$H$_4$); 3.96 (s, 3H,CH$_3$)

EXAMPLE 8

Preparation of Compound 8

A solution of acetylsalicyoyl chloride (1.1 g; 1.1 equivalent) in dichloromethane (15 mL) was added dropwise to a solution of trans,trans-2,4-hexadiene-1-ol (0.574 g; 5.1 mmol) also in dichloromethane (15 mL) and triethylamine (4 mL) at 0° C. After overnight stirring at r.t. the mixture was evaporated to dryness. The residue was taken up in ethyl acetate and extracted with water. The organic phase was dried over sodium sulfate, filtered and evaporated to dryness. The crude product was purified by column chromatography using ethyl acetate/n-hexane (1:5) as eluent. After evaporation, the trans,trans-2,4-hexadiene-1-oxi ester of the acetylsalicylic acid was obtained as an oil (0.99 g; 75% yield). $^1$H NMR (CDCl$_3$; 300 MHz): 7.95 (d,1H,J=7.8 Hz, Harom); 7.49-7.44 (m, 1H, Harom); 7.22 (t,1H,J=7.5 Hz, J=7.5 Hz, Harom); 7.01 (d, 1H,J=8.1 Hz, Harom); 6.28-6.20 (m, 1H, H diene); 5.99 (t, 1H, J=14.4 Hz, J=11.4 Hz, H diene); 5.76-5.58 (m 2H, H diene); 4.71 (d, 2H, J=6.6 Hz, CH$_2$); 2.24 (s, 3H, CH$_3$OAc); 1.69 (d, 3H, J=6.6 Hz, CH$_3$).

A solution of this diene ester (0.4 g; 1.54 mmol), Me$_3$NO (0.3 g; 2 equivalents) and Fe(CO)$_5$ (0.20 mL; 1 equivalent) in THF was stirred at r.t. overnight. The resulting mixture was filtered, and evaporated to dryness to give a dark red oil of compound 8 (0.39 g; 62% yeild). IR (KBr pellet, cm$^{-1}$): 2046 (s), 1954 (s), 1928 (s), 1770 (s), 1722 (s). $^1$H NIMR (CD$_3$OD); 300 MHz): 7.94-7.91 (m,1H, H arom); 7.58-7.52 (m, 1H, H arom); 7.32-7.27 (m, 1H, H arom); 7.09-7.07 (m, 1H, H arom); 6.30-6.25 (m, 1H, H diene); 6.04-6.01 (m, 1H, H diene); 5.77-5.62 (m, 2H, H diene); 4.69 (d, 2H, J=6.0 Hz, CH$_2$); 2.20 (s, 3H, CH$_3$OAc); 1.70 (d, 3H, J=6.0 Hz, CH$_3$).

EXAMPLE 9

Preparation of p-CD/Cp*Mo(CO)$_3$Cl 6

A solution of β-CD hydrate (1.36 g, 1.20 mmol) in water (18.5 ml) was treated with a solution of Cp*Mo(CO)$_3$Cl (0.42 g, 1.20 mmol) in CH$_2$Cl$_2$ (8 ml) and the mixture kept at 60° C. for 6 h. After evaporation of the CH$_2$Cl$_2$ and addition of ethanol (4 ml), the mixture was stirred for 12 h at room temperature. The suspension was filtered and the pale red powder washed several times with $CH_2Cl_2$, water and vacuum dried. Yield: 80%

In summary, various effects of CO have been demonstrated, however, the ways the amount of CO can be increased in the body remain limited. Thus, this invention includes several embodiments to alleviate this problem. One embodiment is directed to a new way of administration of CO by means of compounds having ability to release CO either because they comprise CO (Classes 1,2,3, 4, and 5) or because they are able to generate CO (classes 6 and 7). The preferred use of these compounds (that is any compound having the ability to release CO) is as an anti-inflammatory agent. However, releasing of CO may be used for other indications. Among the compounds of the invention, all are not already known. The new compounds include those comprising complexes linked to another pharmacologically important molecule (Classes 2 and 5).

What is claimed is:

1. A pharmaceutical composition for the release of carbon monoxide (CO) in vivo, comprising:

a complex of the formula:

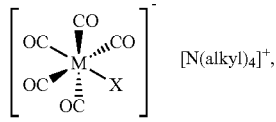

wherein:
M=Mo;
X=Cl, Br, I, OR, SR, carboxylate, or a sugar; and
R=alkyl or aryl; or

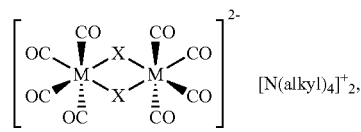

wherein:
M=Mo;
X=OR or SR; and
R=alkyl or aryl; or

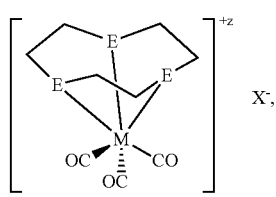

wherein:
M=Mo;
each E is independently N, S, or O:
X=halide or a weakly coordinating anion; and
Z=+1); or

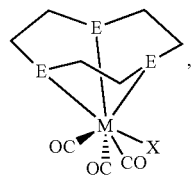

wherein:
M=Mo;
each E is independently N, S, or O:
X=halide, pseudohalide, OR, SR, or carboxylate wherein the pseudohalide is a thiocyanate, cyanate, cyanide, or azide; and
R=alkyl or aryl; or

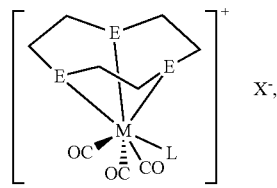

wherein:
M=Mo;
each E is independently N, S, or O:
L=CO, olefin, alkyne, or a monodentate 2-electron donor of O, S, N, or P; and
X=halide or a weakly coordinating anion; or

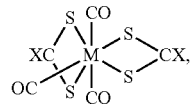

wherein:
M=Mo;
X=$NR_2$ or OR; and
R=alkyl or aryl; or

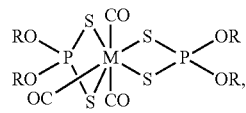

wherein:
M=Mo; and
R=alkyl or aryl; or

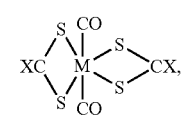

wherein:
M=Mo;
X=$NR_2$ or OR; and
R=alkyl or aryl; or

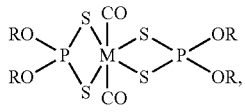

wherein:
  M=Mo; and
  R=alkyl or aryl; or

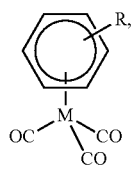

wherein:
  M=Mo; and
  R=alkyl, acyl, formyl, carboxylate, sugar, peptide, or halide; and a pharmaceutically acceptable carrier.

2. The pharmaceutical composition of claim 1, comprising a complex of the formula:

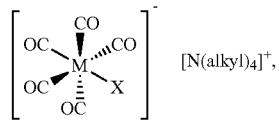

wherein:
  M=Mo;
  X=Cl, Br, I, OR, SR, carboxylate, or a sugar; and
  R=alkyl or aryl.

3. A method for treating a disease in a mammal, wherein said method comprises the step of delivering to said mammal a safe and effective amount of a pharmaceutical composition of claim 1, wherein the disease is selected from the group consisting of an inflammatory disease, a disease with a strong inflammatory component, asthma, injury, infarction, and a circulatory disease.

4. The method of claim 3, wherein the disease with a strong inflammatory component is atherosclerosis, stroke, a coronary disease, or Alzheimer's disease.

5. The method of claim 3, wherein the disease is a chronic inflammatory disease.

6. The method of claim 5, wherein the chronic inflammatory disease is rheumatoid arthritis.

7. The method of claim 3, wherein the mammal is a human.

\* \* \* \* \*